US00RE49006E

(19) United States
(12) Reissued Patent
Popp et al.

(10) Patent Number: US RE49,006 E
(45) Date of Reissued Patent: Apr. 5, 2022

(54) TANK-MIX FORMULATIONS

(71) Applicant: Syngenta Participations AG, Basel (CH)

(72) Inventors: Christian Popp, Münchwilen (CH); Anke Buchholz, Stein (CH); Fabienne Hatt, Basel (CH)

(73) Assignee: Syngenta Participations AG, Basel (CH)

(21) Appl. No.: 16/591,106

(22) Filed: Oct. 2, 2019

Related U.S. Patent Documents

Reissue of:
(64) Patent No.: 9,949,476
Issued: Apr. 24, 2018
Appl. No.: 14/891,774
PCT Filed: May 21, 2014
PCT No.: PCT/EP2014/060410
§ 371 (c)(1),
(2) Date: Nov. 17, 2015
PCT Pub. No.: WO2014/187847
PCT Pub. Date: Nov. 27, 2014

(30) Foreign Application Priority Data

May 23, 2013 (EP) ..... 13168923

(51) Int. Cl.
*A01N 25/32* (2006.01)
*A01N 43/90* (2006.01)
*A01N 43/34* (2006.01)

(52) U.S. Cl.
CPC ..... *A01N 25/32* (2013.01); *A01N 43/90* (2013.01); *A01N 43/34* (2013.01)

(58) Field of Classification Search
CPC ..... A01N 25/32; A01N 43/90; A01N 43/34
See application file for complete search history.

(56) References Cited

U.S. PATENT DOCUMENTS 4,506,831 A * 3/1985 Ghyczy ..... A01N 25/04 206/524.1
6,734,141 B2 * 5/2004 Humble ..... A01N 25/30 504/206
9,067,892 B2 * 6/2015 Muehlebach ..... A01N 47/06
9,414,597 B2 * 8/2016 Buchholz ..... A01N 47/40
9,560,851 B2 * 2/2017 Buchholz ..... A01N 43/90
9,603,367 B2 * 3/2017 Buchholz ..... A01N 47/06
9,686,992 B2 * 6/2017 Buchholz ..... A01N 43/58
2003/0104944 A1 * 6/2003 Humble ..... A01N 25/30 504/206
2007/0213226 A1 * 9/2007 Sieverding ..... A01N 53/00 504/206
2012/0220464 A1 8/2012 Giessler-Blank et al.
2016/0081342 A1 * 3/2016 Popp ..... A01N 47/06 514/278
2019/0307127 A1 * 10/2019 Gewehr ..... A01N 43/90
2020/0131181 A1 * 4/2020 Jones ..... A01N 43/90
2020/0131182 A1 * 4/2020 Jones ..... C07D 471/10

FOREIGN PATENT DOCUMENTS

EP 2999334 B1 4/2019
WO WO2010/066780 A1 6/2010
WO WO2011/151199 A1 12/2011

OTHER PUBLICATIONS

Communication from the Examining Division and Annex to the communication dated Dec. 11, 2017 in granted European counterpart application EP2999334B1.
Reply to communication from the Examining Division dated Jun. 21, 2018 in granted European counter-part application EP2999334B1.
Spanoghe et al., "Effect of adjuvants on atomization of pesticides", Atomization and Sprays, vol. 14, No. 6, pp. 511-524 (2004).*
International Search Report and Written Opinion for International Application No. PCT/EP2014/060410 dated Jul. 1, 2014.

* cited by examiner

*Primary Examiner* — Jerry D Johnson
(74) *Attorney, Agent, or Firm* — BakerHostetler; Toni-Junell Herbert

(57) ABSTRACT

The invention relates to the use of additives in the preparation of crop protection composition spray mixtures, in particular as additives for tank mixtures of specific pesticides according to formula (I), pesticide mixtures and crop protection compositions comprising these pesticides.

(I)

6 Claims, No Drawings

TANK-MIX FORMULATIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION INFORMATION

This application is a *reissue of U.S. Pat. No. 9,949,476, which is a* 371 of International Application No. PCT/EP2014/060410, filed 21 May 2014, which claims priority to European Patent Application No. 13168923.4, filed 23 May 2013, the contents of all of which are incorporated [herein] by reference herein.

BACKGROUND TO THE INVENTION

The invention relates to the use of additives in the preparation of crop protection composition spray mixtures, in particular as additives for tank mixtures of specific tetramic acid pesticides according to formula (I).

The tetramic acid pesticides referred to herein are the pesticides of formula (I)

(I)

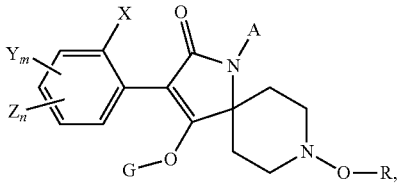

wherein

X, Y and Z independently of each other are $C_{1-4}$alkyl, $C_{3-6}$cycloalkyl, $C_{1-4}$haloalkyl, $C_{1-4}$alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, ammonium, sulfonium or a latentiating group;

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl or a group selected from G; and A is hydrogen, $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{2-6}$haloalkenyl, $C_{3-6}$alkynyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di($C_{1-6}$alkyl)carbamoyl, benzoyl, $C_{1-6}$alkylsulfonyl, phenylsulfonyl, $C_{1-4}$alkylthio($C_{1-4}$)alkyl, $C_{1-4}$alkylsulfinyl($C_{1-4}$)alkyl or $C_{1-4}$alkylsulfonyl($C_{1-4}$)alkyl;

Or A is O-$A^1$ where $A^1$ is selected from one of A, as defined above, or furanyl -($C_{1-4}$)alkyl, tetrahydro-thiofuranyl, tetrahydro-thiopyranyl or 1-($C_{1-4}$)alkoxy-piperidin-4-yl or an agrochemically acceptable salt or an N-oxide thereof.

The compounds of formula (I) above have insecticidal properties. These compounds have a systemic mode of action. They penetrate the leaf cuticle and enter the plant's vascular system, moving both upwards and downwards via phloem and xylem to new shoot, leaf and root tissues. This "2-way systemicity" results in effective control of hidden pests on above- and below-ground plant parts and on new growth. Insects ingest the active ingredient by feeding on the plant. The efficacy of the compounds according to formula (I) i.e. increased uptake can be enhanced when formulating the active ingredient into a composition suitable for application on crops.

One type of formulation often used for agrochemical active ingredients are suspension concentrates. Suspension concentrate formulations are stable suspensions of solid pesticide(s) in a fluid usually intended for dilution before use. Ideally, the suspension should be stable (i.e. not settle out). Suspension concentrate formulations are generally diluted with water prior to customary spraying via nozzles. Other common types of formulations include soluble powders (SP), water soluble granules (SG), water dispersible granules (WG), wettable powders (WP), emulsifiable concentrates (EC), and dispersible concentrates (DC), emulsion in water (EW), oil dispersion (OD), or soluble liquid (SL). Besides the active substance(s) (or also called active ingredient(s)), also other auxiliaries, such as Surfactants, emulsifiers, dispersants, wetting agents, antifreezes, antifoams, biocides, solvents, stabilizer, anti-microbials, pigments, buffers, surface-active substances etc. can be present in the formulation; such substances are known to the person skilled in the art of formulation.

In crop protection, additives, also called adjuvants or penetrants, are usually used to improve the efficacy of crop protection composition active ingredients. The adjuvants are capable of penetrating the wax layer on the leaves of the plant thereby allowing systemic active ingredients increased access to the epidermal cells of the plant.

These are either added to the aqueous spray mixture shortly before spraying separately to the crop protection composition (as tank mixture adjuvants) or incorporated directly into the crop protection composition concentrate together with other auxiliaries (a built-in formulation).

Tank mixture adjuvants are added to the water in the same tank separately from the formulated active ingredient and are distributed within the entire spray mixture by stirring.

The tank mixture adjuvants can be added to water before or after the formulated active ingredient.

Many different types of tank mixture adjuvants are known to the person skilled in the art of agrochemical formulations e.g. mineral oils, vegetable oils, trans-esterified vegetables oils, polysiloxanes, non-ionic organic surfactants, ionic surfactants, buffering (or acidifying) agents, or polymers such as Nufilm 17, which is an emusifiable film forming polymer based on natural Pinolene or other polymers, based on Terpenes.

However, the formulation of tetramic acid compounds according to formula (I), involves more challenges than just the simple improvement of its efficacy with adjuvants. An overdose of tetramic acid compounds (ACCase chemistry) could lead to phytotoxic reactions in sensitive plant species. It is well known that different acetyl-CoA carboxylase isoforms exist across higher plants. The completely different structure of ACCase isoforms in Gramineae and dicotyledonous plants could for example explain different sensitivities towards tetramic acid compounds (e.g. ACCase herbicides) (see Konishi et al. (1996) Plant Cell Physiol. 37,117-122 and Schulte et al. (1997) Proc. Natl. Acad. Sci. U.S.A.

94, 3456-3470). But also across dicotyledonous crops different sensitivities across plant families (e.g. Brassicacea; see Price et al. (2003) Biochem. J. 375, 415-423) could exist.

However, usually when applying known tank-mix additives (also referred to herein as tank mixture adjuvants or tank-mix adjuvants) to reduce phytotoxicity, the efficacy of the tetramic acid compound is usually compromised. When applying tank-mix additives known to increase efficacy, it is known that phytoxicity is usually positively correlated i.e. the higher the efficacy, the higher the phytoxicity risk and vice versa. The lower the efficacy, the lower the phytoxic risk.

Thus, the technical problem to be solved is finding a suitable tank-mix adjuvant that will reduce any potential phytoxicity of the tetramic acid according to formula (I) to an acceptable level, whilst simultaneously at least maintaining, if not maximising, the efficacy of the tetramic acid according to formula (I).

The solution to this problem was not obvious, since most adjuvants that increase efficacy, would generally also cause an increase in the compounds' inherent phytoxicity. Furthermore, the tank-mix of the compounds of formula (I) and the selected tank-mixture adjuvants must ensure that the tetramic acid compounds according to formula (I) are predominantly in their keto-enol form when sprayed on the field.

It has been found that surprisingly polysiloxanes adjuvants are very suitable as tank-mix adjuvants for the tetramic acid compounds according to the invention. Surprisingly, these polysiloxane adjuvants solve the two main problems of the tetramic acids mentioned above i.e. acceptable phytotoxicity and maximum efficacy. Other adjuvants known to the skilled person have failed to solve the two problems adequatly.

The use of these spreading polysiloxane surfactants, such as, for example, BREAK-THRU® S-240 or BREAK-THRU® S-233, from Evonik GmbH, in combination with a pesticide used as an improvement in the pesticide uptake by the plant and generally to an increase in its effectiveness or its efficacy is known. U.S. Pat. No. 6,734,141 describes that especially a low surface tension and not necessarily the spreading is responsible for this increase in efficacy. However, there has never been an indication that compositions such as Break-Thru enable the reduction of phytoxicity of tetramic acid compounds according to formula (I).

The non-expert will maybe assume that all commercial wetting agents or tensides (e.g. in cosmetic uses or as component of household cleaning compositions) will promote the efficacy of pesticides. This is wrong and has been shown in several publications e.g. in Pesticide Formulation and Adjuvant Technology, edited by Chester L. Foy and David W. Pritchard. CRC Press LLC, 1996, pp. 323-349).

It is therefore still surprising and not apparent that the substances of the present invention can reduce the phytotoxicity of the tetramic acid pesticides according to formula (I) whilst maintaining and even improving the efficacy of the active ingredients. Within the context of the invention, numerous adjuvants were tested; of these, surprisingly, specifically only polysiloxanes proved to be suitable.

Two other surprisingly good adjuvants for this chemistry class were Geropon® DOS-PG and Trend® 90. Unexpectedly these also reduced the phytotoxicity, whilst providing increased the efficacy of the tetramic acid compounds of formula (I).

SUMMARY OF THE INVENTION

The invention is thus a composition comprising a tetramic acid compound of the formula (I)

(I)

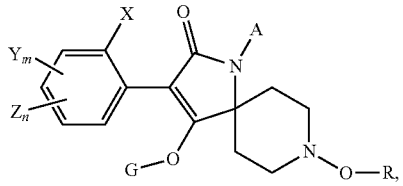

wherein

X, Y and Z independently of each other are $C_{1-4}$alkyl, $C_{1-4}$cycloalkyl, $C_{1-4}$haloalkyl, $C_{1-4}$alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, ammonium, sulfonium or a latentiating group;

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl or a group selected from G; and A is hydrogen, $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{2-6}$haloalkenyl, $C_{3-6}$alkynyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di($C_{1-6}$alkyl)carbamoyl, benzoyl, $C_{1-6}$alkylsulfonyl, phenylsulfonyl, $C_{1-4}$alkylthio($C_{1-4}$)alkyl, $C_{1-4}$alkylsulfinyl($C_{1-4}$)alkyl or $C_{1-4}$alkylsulfonyl($C_{1-4}$)alkyl;

Or A is O-$A^1$ where $A^1$ is selected from one of A, as defined above, or furanyl-($C_{1-4}$)alkyl, tetrahydro-thiofuranyl, tetrahydro-thiopyranyl or 1-($C_{1-4}$)alkoxy-piperidin-4-yl;

or an agrochemically acceptable salt or an N-oxide of formula (I);

and a tank-mix adjuvant selected from one or more polysiloxane(s), Geropon® and Trend®90. Preferably the tank-mix adjuvant is selected from one or more polysiloxane(s). More preferably, the polysiloxane(s) can be selected from one or more of the following commercially available products:

BREAK-THRU® S-240 from Evonik GmbH
BREAK-THRU® S-233 from Evonik GmbH (also known as Complement Super® or Etalfix Pro®)
BREAK-THRU® OE441 from Evonik GmbH
BREAK-THRU® OE444 from Evonik GmbH
BREAK-THRU® OE440 from Evonik GmbH
BREAK-THRU® S200 from Evonik GmbH
BREAK-THRU® S243 from Evonik GmbH
BREAK-THRU® S278 from Evonik GmbH
BREAK-THRU® S279 from Evonik GmbH
Advance® from Evonik GmbH
Union® from Evonik GmbH
Silwet® L77 from Moventis Performance Material
Silwet® 408 from Moventis Performance Material
Silwet® 806 from Moventis Performance Material
Silwet® 625 from Moventis Performance Material
Silwet® ECO from Moventis Performance Material
Silwet® 618 from Moventis Performance Material
Silwet® 719 from Moventis Performance Material Silwet® 7500 from Moventis Performance Material
Silwet® 560 from Moventis Performance Material
Silwet® 641 from Moventis Performance Material
Silwet® HS312 from Moventis Performance Material
Silwet® HS429 from Moventis Performance Material
Silwet® HS508 from Moventis Performance Material
Silwet® HAS604 from Moventis Performance Material
Silwet® 7280 from Moventis Performance Material
AgroSpred® 730 from Moventis Performance Material
Sylgard® 309 from Dow AgroScience
Q2-5211 from Dow AgroScience The invention also covers a combination pack comprising a combination of a compound according to formula (I) and a tank-mix adjuvant selected from one or more polysiloxanes wherein a first container contains the compound according to formula (I) and a second container contains the adjuvant selected from one or more polysiloxane(s), Geropon® DOS-PG and Trend®90. Preferably the tank-mix adjuvant is selected from one or more polysiloxane(s). More preferably, the polysiloxane(s) can be selected from one or more of the above-mentioned commercially available products.

Furthermore, the invention covers the use of a polysiloxane, Geropon® DOS-PG or Trend®90 as a tank-mix adjuvant for a pesticidal composition comprising a tetramic acid compound of the formula (I). Preferably the tank-mixt adjuvant is selected from one or more polysiloxane(s). More preferably, the polysiloxane(s) can be selected from one or more of the above-mentioned commercially available products.

In addition, the invention covers a method of increasing the efficacy and reducing the phytoxicity of pesticidally active tetramic acid compounds according to formula (I), by adding a tank-mix adjuvant selected from one or more polysiloxane(s), Geropon® DOS-PG and Trend®90 to the tetramic acid compounds prior to applying the pesticidally active compounds to the crops. Preferably the tank-mixt adjuvant is selected from one or more polysiloxane(s). More preferably, the polysiloxane(s) can be selected from one or more of the above-mentioned commercially available products.

A method of combating and controlling pests which comprises applying to a pest, to a locus of a pest, or to a plant susceptible to attack by a pest a composition according to the invention.

A method of combating and controlling pests which comprises the following steps:

a) Obtaining either a polysiloxane adjuvant, Geropon® DOS-PG or Trend®90 and a formulated tetramic acid compound according to formula (I) as defined in claim 1 or claim 2;
b) Mixing the formulated tetramic acid compound according to formula (I) with the adjuvant to prepare a pesticidal composition for application on a crop
c) Applying the resulting composition to a pest, to a locus of a pest, or to a plant susceptible to attack by a pest;

wherein preferably the tetramic acid compound in step a is formulated as a suspension concentrate, emulsion concentrate, wettable powder, water dispersible granule, soluble granule or soluble powder. Preferably the tank-mix adjuvant is selected from one or more polysiloxane(s). More preferably, the polysiloxane(s) can be selected from one or more of the above-mentioned commercially available products.

Geropon® DOS-PG is defined herein as sodium dioctylsulphosuccinate.

Trend®90 is defined herein as isodecyl alcohol ethoxylate.

In all of the embodiments of the invention, the tetramic acid compound of Formula (I) can be formulated as as a suspension concentrate, emulsion concentrate, wettable powder, oil dispersion, emulsion in water, soluble liquid, water dispersible granule, soluble granule or soluble powder.

DETAILED DESCRIPTION OF THE INVENTION

Compounds of Formula (I)

In the compounds of formula (I), each alkyl moiety either alone or as part of a larger group is a straight or branched chain and is, for example, methyl, ethyl, n-propyl, n-butyl, iso-propyl, sec-butyl, iso-butyl, and tert-butyl.

Alkoxy groups preferably have a preferred chain length of from 1 to 4 carbon atoms. Alkoxy is, for example, methoxy, ethoxy, propoxy, iso-propoxy, n-butoxy, iso-butoxy, sec-butoxy and tert-butoxy. Such groups can be part of a larger group such as alkoxyalkyl and alkoxyalkoxyalkyl. Alkoxyalkyl groups preferably have a chain length of 1 to 4 carbon atoms. Alkoxyalkyl is, for example, methoxymethyl, methoxyethyl, ethoxymethyl, ethoxyethyl, n-propoxymethyl, n-propoxyethyl or iso-propoxymethyl.

Halogen is generally fluorine, chlorine, bromine or iodine. This also applies, correspondingly, to halogen in combination with other meanings, such as haloalkyl or haloalkoxy.

Haloalkyl and haloalkoxy groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1 -difluoro -2,2,2-trichloroethyl, 2,2,3,3 -tetrafluoroethyl and 2,2,2-trichloroethyl; preferably trichloromethyl, difluorochloromethyl, difluoromethyl, trifluoromethyl and dichlorofluoromethyl. Haloalkoxy is, for example, fluoromethoxy, difluoromethoxy, trifluoromethoxy, chloromethoxy, dichloromethoxy, trichloromethoxy, 2,2,2-trifluoroethoxy, 2-fluoroethoxy, 2-chloroethoxy, pentafluoroethoxy, 1,1-difluoro-2,2,2-trichloroethoxy, 2,2,3,3-tetrafluoroethoxy and 2,2,2-trichloroethoxy; preferably trichloro-methoxy, difluorochloromethoxy, difluoromethoxy, trifluoromethoxy and dichlorofluoromethoxy.

The latentiating groups G are selected to allow its removal by one or a combination of biochemical, chemical or physical processes to afford compounds of formula (I) where G is hydrogen before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Such latentiating groups are known in the art, for example, from WO08/071405, WO09/074314, WO09/049851, WO10/063670 and WO10/066780. The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur; start proof $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl , $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1C_5$alkylcarbonyl-N—$C_1C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$,alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_5$cyanoalkyl, $C_1$-$C_{10}$nitroalkyl, $C_2$-$C_{10}$aminoalkyl , $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$_3$alkyl-thio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_5$dialkylamino $R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl , $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy, $C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and R" is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl , $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio , $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$ -C, alkylthio , $C_1$-$C_3$alkylsulfinyl, $C_1$-$C_3$ alkylsulfonyl, halogen, cyano or by nitro), phenoxy$C_7$-$C_5$alkyl (wherein wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$akylsulfinyl, $C_1$-$C_3$ alkylsulfonyl, halogen, cyano or by nitro), $C_3$-$C_5$-haloalkenyl, $C_1$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

In one embodiment, the latentiating group G is selected from the group —C(=O)—$R^a$ and —C(=O)—O—$R^b$; wherein $R^a$ is selected from hydrogen, $C_1$-$C_{12}$alkyl, $C_2$-$C_{12}$alkenyl, $C_2$-$C_{12}$alkynyl, $C_1$-$C_{10}$haloalkyl and $R^b$ is selected from $C_1$-$C_{12}$alkyl, $C_2$-$C_{12}$alkenyl, $C_2$-$C_{12}$alkynyl and $C_1$-$C_{10}$haloalkyl. In particular, $R^a$ and $R^b$ are selected from the group consisting of methyl, ethyl, n-propyl, isopropyl, n-butyl, iso-butyl, sec-butyl, tert-butyl, ethenyl and propenyl, e.g. 2-propen-1-yl.

It is preferred that G is hydrogen, a metal, preferably an alkali metal or alkaline earth metal, or an ammonium or sulfonium group, where hydrogen is especially preferred.

Depending on the nature of the substituents, compounds of formula (I) may exist in different isomeric forms. When G is hydrogen, for example, compounds of formula (I) may exist in different tautomeric forms:

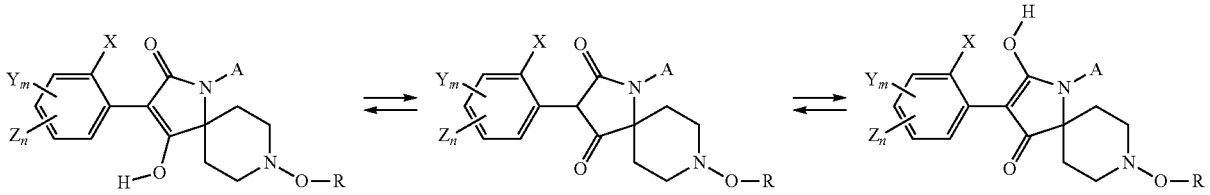

This invention covers all isomers and tautomers and mixtures thereof in all proportions. Also, when substituents contain double bonds, cis- and trans-isomers can exist. These isomers, too, are within the scope of the claimed compounds of the formula (I).

The invention relates also to the agriculturally acceptable salts which the compounds of formula (I) are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methyl-nonylamine, methylpentadecylamine, methyloctadecylamine, ethylbutylamine, ethylheptyl-amine, ethyloctylamine, hexylheptylamine, hexyloctylamine, dimethylamine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula $[N(R_a R_b R_c R_d)]OH$, wherein $R_a$, $R_b$, $R_c$ and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_eR_fR_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

The compounds of the invention may be made by a variety of methods as described in detail, for example, in WO09/049851, WO10/063670 and WO10/066780.

It should be understood that in those compounds of formula (I), where G is a metal, ammonium or sulfonium as mentioned above and as such represents a cation, the corresponding negative charge is largely delocalised across the O—C═C—C═O unit.

The compounds of formula (I) according to the invention also include hydrates which may be formed during the salt formation.

Preferably, in the compounds of the formula (I), the substituent R is hydrogen, $C_{1-4}$alkyl, $C_{1-4}$haloalkyl, in particular methyl, ethyl, iso-propyl, n-propyl, tert-butyl, secbutyl, iso-butyl, or n-butyl.

Preferably, X, Y and Z, are selected, independently of one another, from $C_1$-$C_4$alkyl, $C_1$-$C_4$alkoxy or halogen, in particular methyl, ethyl, iso-propyl, n-propyl, methoxy, fluoro, bromo or chloro, when m+n is 1, 2 or 3, in particular, when m+n is 1 or 2.

Alternatively, Y and Z, independently of each other, denote $C_1$-$C_4$alkyl, $C_1$-$C_4$alkoxy, halogen, in particular methyl, ethyl, iso-propyl, n-propyl, methoxy, fluoro, chloro, bromo, when m+n is 1, 2 or 3, in particular, when m+n is 1 or 2.

In a particular embodiment, in the compound of formula (I), when m is 1, Y is in an ortho position and X and Y are each selected independently from the group consisting of methyl, ethyl, iso-propyl and n-propyl.

In another embodiment, preferably combined with the previous embodiment, wherein when n is 1 in the compound of formula (I), Z is in the para position and is selected from the group consisting of fluoro, bromo and chloro, methyl, ethyl, iso-propyl and n-propyl. Preferably, Z is methyl, fluoro, bromo and chloro. More preferably, Z is chloro or methyl.

In another embodiment, wherein in the compound of formula (I), m and n are each 1, Y is in an ortho position and X and Y are selected independently from the group consisting of methyl and ethyl, and Z is in the para position and is selected from the group consisting of fluoro, bromo and chloro. Preferably, X and Y are each in an ortho position and are methyl and preferably Z is in a para position and is chloro or methyl.

In the compounds of the formula (I), the substituent A is preferably hydrogen, $C_{1-4}$alkyl, $C_{1-4}$haloalkyl, $C_{2-4}$alkenyl, $C_{1-4}$alkoxy($C_{1-4}$)alkyl, $C_{1-4}$alkoxy($C_{1-4}$)alkoxy($C_{1-4}$)alkyl, tetrahydrofuranyl, tetrahydropyranyl, in particular methyl, ethyl, n-propyl, iso-propyl, n-butyl, iso-butyl, sec-butyl, and tert-butyl, trifluoromethyl, 2,2,2-trifluoroethyl, 2,2-difluoroethyl, 2-fluoroethyl, allyl, methoxymethyl, ethoxymethyl, methoxyethyl, methoxypropyl, methoxyethoxymethyl, methoxymethoxyethyl, tetrahydrofuran-2-yl, tetrahydropyran-2-yl, tetrahydrofuran-3-yl, tetrahydropyran-4-yl.

In one embodiment, A is preferably hydrogen.

In another embodiment, A is preferably $C_{1-4}$alkyl. In a preferred embodiment, A is selected from the group consisting of methyl, ethyl, n-propyl, iso-propyl, n-butyl, iso-butyl, sec-butyl, tert-butyl, methoxymethyl, ethoxymethyl and methoxyethyl.

In yet another embodiment, A is preferably selected from the group O-$A^1$, wherein $A^1$ is selected from the group consisting of hydrogen, methyl, ethyl, n-propyl, iso-propyl, n-butyl, iso-butyl, tert-butyl, methoxymethyl, ethoxymethyl, methoxyethyl, methoxypropyl, tetrahydrofuran-2-yl, tetrahydropyran-2-yl, tetrahydrofuran-3-yl and tetrahydropyran-4-yl.

Preferably, when A is O-$A^1$, $A^1$ is hydrogen, methyl, ethyl, methoxymethyl, and tetrahydrofuran -2-yl. Even more preferably, when A is O-$A^1$, $A^1$ is methyl or ethyl. Most preferably, when A is O-$A^1$, $A^1$ is methyl.

In another preferred group of compounds of the formula (I), R is one of hydrogen, methyl, ethyl or trifluoroethyl, trifluoromethyl, X is methyl, ethyl or methoxy, Y and Z, independently of each other, are methyl, ethyl, methoxy, fluoro, chloro or bromo, G is hydrogen or —(C═O)$OCH_2CH_3$ and A has the meanings assigned to it above.

In a particularly preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, or bromo, G is hydrogen or —(C═O)$OCH_2CH_3$ and A has the meanings assigned to it above.

In a more preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, bromo, G is hydrogen or —(C═O)$OCH_2CH_3$ and A is hydrogen, methyl, ethyl, isopropyl, trifluoromethyl, 2,2,2-trifluoroethyl, 2,2-difluoroethyl, 2-fluoroethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, methoxymethyl, ethoxymethyl, methoxyethyl, methoxypropyl, methoxyethoxymethyl, methoxymethoxyethyltetrahydrofuran-2-yl, tetrahydropyran-2-yl, tetrahydrofuran-3-yl, or tetrahydropyran-4-yl.

In a another preferred group of compounds of the formula (I), R is methyl, X is methyl or methoxy, Y and Z, independently of each other, are methyl, ethyl, methoxy, chloro or bromo, G is hydrogen, methoxycarbonyl or propenyloxycarbonyl or —(C═O)$OCH_2CH_3$, and A is hydrogen, methyl, ethyl, methoxy, ethoxy, methoxymethyl, tetrahydrofuran-2-yl or tetrahydrofuran-3-yl.

In a another preferred group of compounds of the formula (I), R is methyl, X is methyl or methoxy, Y and Z, independently of each other, are methyl, ethyl, methoxy, chloro or bromo, m is 1, n is 1, G is hydrogen, methoxycarbonyl or propenyloxycarbonyl or —(C═O)$OCH_2CH_3$, and A is hydrogen, methyl, ethyl, methoxymethyl, tetrahydrofuran-2-yl or tetrahydrofuran-3-yl.

In another preferred group of compounds of the formula (I), A is hydrogen or $C_{1-4}$alkyl or $C_{1-4}$alkoxy, m is 1, n is 1, X is methyl, Y is in the ortho position and is methyl, Z is in the para position and is methyl, G is hydrogen or —(C═O)$OCH_2CH_3$, R is methyl.

In a more preferred group of compounds of the formula (I), A is hydrogen, m is 1, n is 1, X is methyl, Y is in the ortho position and is methyl, Z is in the para position and is methyl, G is hydrogen or —(C═O)$OCH_2CH_3$, R is methyl.

In a more preferred group of compounds of the formula (I), A is methyl, m is 1, n is 1, X is methyl, Y is in the ortho position and is methyl, Z is in the para position and is methyl, G is hydrogen or —(C═O)$OCH_2CH_3$, R is methyl.

In a more preferred group of compounds of the formula (I), A is methoxy, m is 1, n is 1, X is methyl, Y is in the ortho position and is methyl, Z is in the para position and is methyl, G is hydrogen or —(C═O)$OCH_2CH_3$, R is methyl.

In a more preferred group of compounds of the formula (I), A is ethoxy, m is 1, n is 1, X is methyl, Y is in the ortho position and is methyl, Z is in the para position and is methyl, G is hydrogen or —(C═O)$OCH_2CH_3$, R is methyl.

In another preferred group of compounds of the formula (I), A is hydrogen or $C_{1-4}$alkyl or $C_{1-4}$alkoxy, m is 1, n is 1, X is methyl, Y is in the ortho position and is methyl, Z is in the para position and is chloro, G is hydrogen or —(C═O)$OCH_2CH_3$, R is methyl.

In a more preferred group of compounds of the formula (I), A is hydrogen, m is 1, n is 1, X is methyl, Y is in the ortho position and is methyl, Z is in the para position and is chloro, G is hydrogen or —(C═O)$OCH_2CH_3$, R is methyl.

In a more preferred group of compounds of the formula (I), A is methyl, m is 1, n is 1, X is methyl, Y is in the ortho position and is methyl, Z is in the para position and is chloro, G is hydrogen or —(C═O)$OCH_2CH_3$, R is methyl.

In a more preferred group of compounds of the formula (I), A is methoxy, m is 1, n is 1, X is methyl, Y is in the ortho position and is methyl, Z is in the para position and is chloro, G is hydrogen or —(C═O)$OCH_2CH_3$, R is methyl.

In a more preferred group of compounds of the formula (I), A is ethoxy, m is 1, n is 1, X is methyl, Y is in the ortho position and is methyl, Z is in the para position and is chloro, G is hydrogen or —(C═O)$OCH_2CH_3$, R is methyl.

Preferably, the compounds of formula (I) are selected from:

(i)

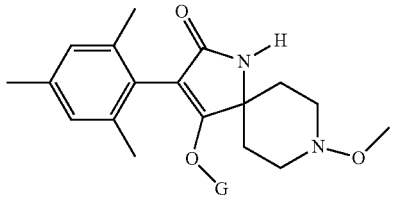

(i')

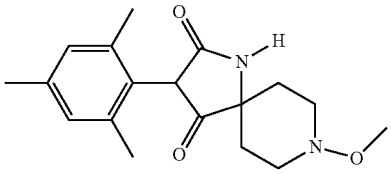

(ii)

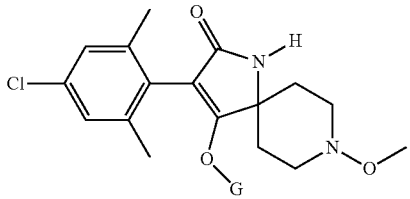

(ii')

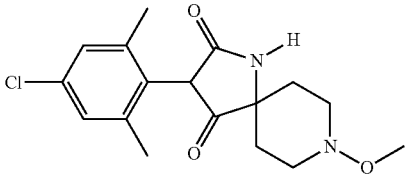

(iii)

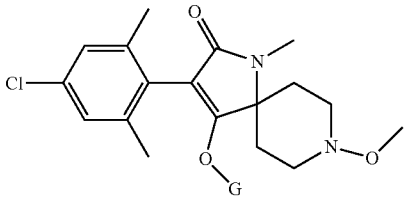

-continued
(iii′)
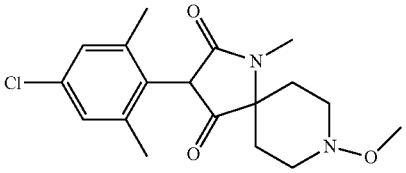
(iv)
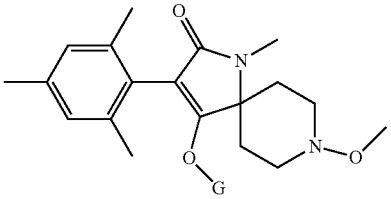
(iv′)
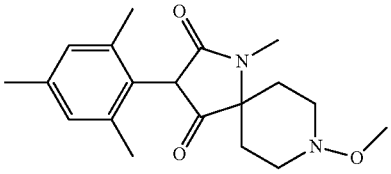
(v)
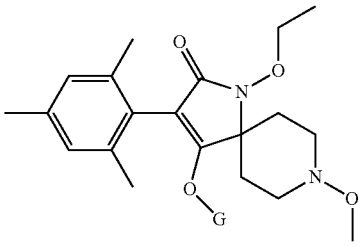
(v′)
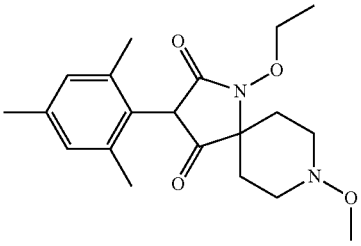
(vi)
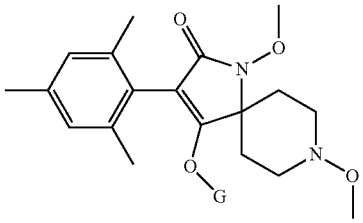
(vi′)
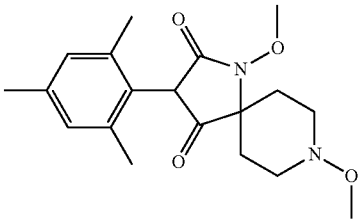
-continued
(vii)
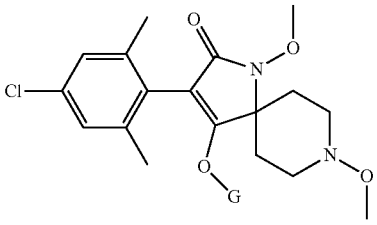
(vii′)
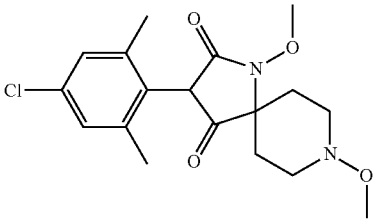
(viii)
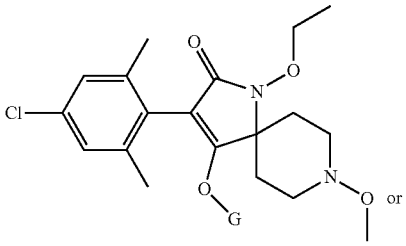
or
(viii′)
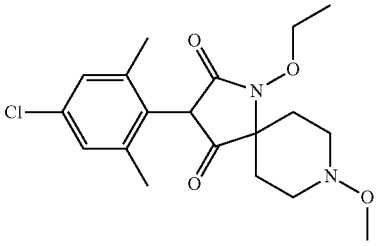
wherein G is
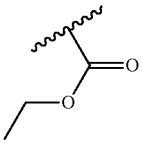
or H.
More preferably, the compounds of formula (I) are selected from:
(i)
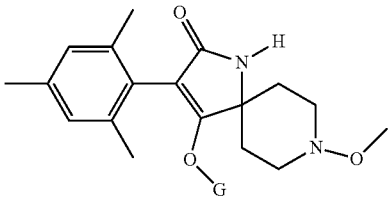

-continued
(i′)
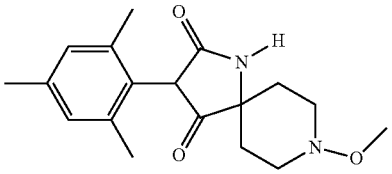
(ii)
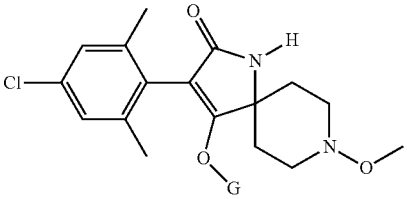
(ii′)
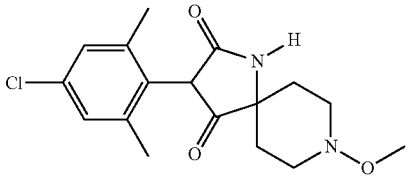
(iii)
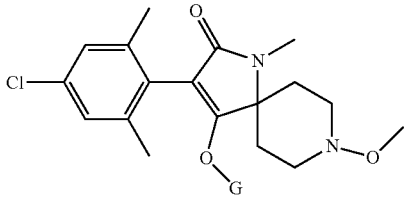
(iii′)
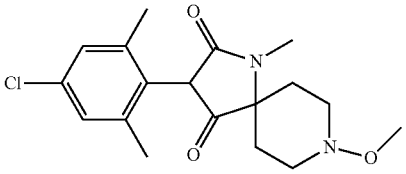
(iv)
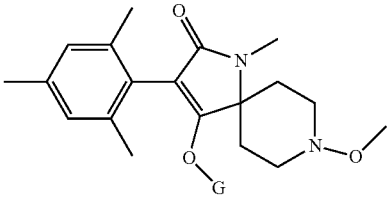
(iv′)
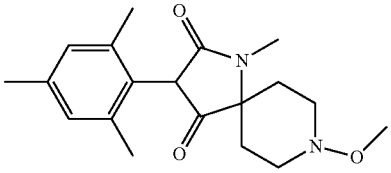
(v)
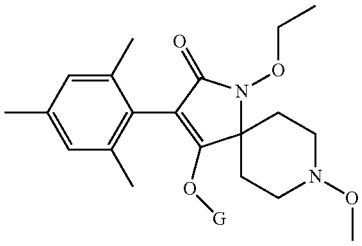
-continued
(v′)
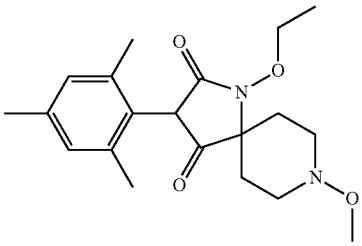
(vi)
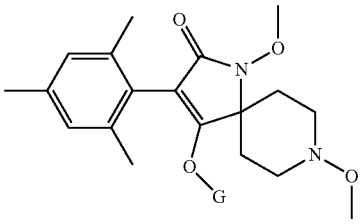
(vi′)
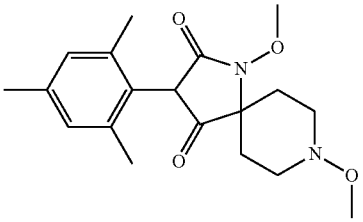
(vii)
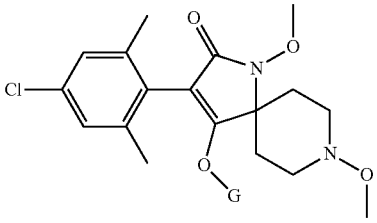
(vii′)
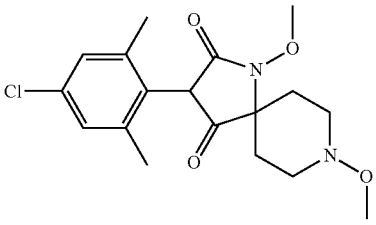
(viii)
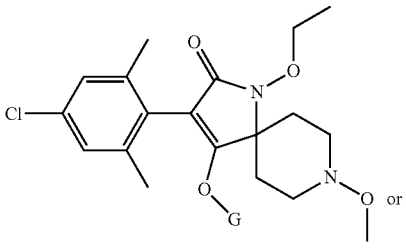
or -continued (viii')

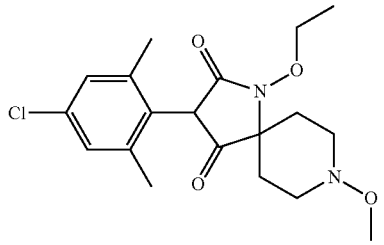

wherein G is

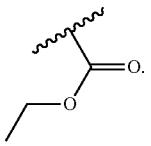

The Tank-Mix Adjuvant

The polysiloxanes which can be used in this invention include in particular also di- and trisiloxanes, organosilicones (also known as organomodified silicones) and hydrophilic polysiloxanes. The polysiloxanes suitable as a tank-mix adjuvant according to the invention are preferably those of formula (II):

(II)

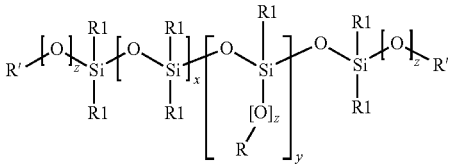

z is 0 or 1
x is a number from 0 to 100
y is 0 or greater
R' is R or an alkyl radical having 1 to 8 carbon atoms or a hydrogen atom
R is $C_nH_{2n}O(C_eH_{2e}O)_pK$ or $Si_nR1_{2n}O(Si_eR1_{2e}O)_pK$
R1 are independently alkyl, alkenyl or alkynyl radicals having 1 to 4 carbon atoms or aryl radicals
n is 1, 2, 3 or 4
e is 1, 2, 3 or 4
p is 0 or greater
K is H, an alkyl radical having at most 4 carbon atoms or $SiR1_2R2$.

In a preferred embodiment:
x is a number from 0 to 100
y is 0 or greater
R' is R or an alkyl radical having 1 to 8 carbon atoms, preferably 1 to 4 carbon atoms, or a hydrogen atom
R is $C_nH_{2n}O(C_eH_{2e}O)_pK$
R1 are all alkyl radicals having 1 to 4 carbon atoms
n is 1, 2, 3 or 4
e is 1, 2, 3 or 4
p is 0 or greater
K is H or an alkyl radical having at most 4 carbon atoms.

In a more preferred embodiment:
x is a number from 0 to 100
y is 0 or greater
R' is R or an alkyl radical having 1 to 8 carbon atoms, preferably 1 to 4 carbon atoms, or a hydrogen atom
R is $C_nH_{2n}O(C_eH_{2e}O)_pK$
R1 are at least to 80% methyl radicals
n is 1, 2, 3 or 4
e is 1, 2, 3 or 4
p is 0 or greater
K is H or an alkyl radical having at most 4 carbon atoms.

In a most preferred embodiment:

(II')

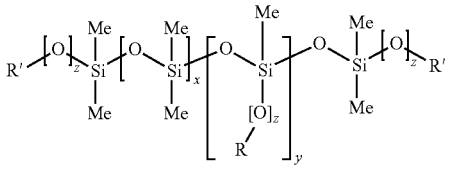

x is a number from 0 to 100
y is 0 or greater
R' is R or an alkyl radical having 1 to 8 carbon atoms, preferably 1 to 4 carbon atoms, or a hydrogen atom
R is $C_nH_{2n}O(C_eH_{2e}O)_pK$
R1 are all methyl radicals
n is 1, 2, 3 or 4
e is 1, 2, 3 or 4
p is 0 or greater
K is H or an alkyl radical having at most 4 carbon atoms.

The polysiloxanes of Formula (II) include in particular also di- and trisiloxanes, organosilicones and hydrophilic polysiloxanes.

Preferably the polysiloxanes that are used are liquid oils, but they can also be used when applied to solid carriers.

Known polysiloxanes that are commercially available include, but are not limited to:
BREAK-THRU® S-240 from Evonik GmbH
BREAK-THRU® S-233 from Evonik GmbH (also known as Complement Super® or Etalfix Pro®)
BREAK-THRU® 0E441 from Evonik GmbH
BREAK-THRU® 0E444 from Evonik GmbH
BREAK-THRU® 0E440 from Evonik GmbH
BREAK-THRU® S200 from Evonik GmbH
BREAK-THRU® S243 from Evonik GmbH
BREAK-THRU® S278 from Evonik GmbH
BREAK-THRU® S279 from Evonik GmbH
Advance® from Evonik GmbH
Union® from Evonik GmbH
Silwet® L77 from Moventis Performance Material
Silwet® 408 from Moventis Performance Material
Silwet® 806 from Moventis Performance Material
Silwet® 625 from Moventis Performance Material
Silwet® ECO from Moventis Performance Material
Silwet® 618 from Moventis Performance Material
Silwet® 719 from Moventis Performance Material
Silwet® 7500 from Moventis Performance Material
Silwet® 560 from Moventis Performance Material
Silwet® 641 from Moventis Performance Material
Silwet® HS312 from Moventis Performance Material
Silwet® HS429 from Moventis Performance Material
Silwet® HS508 from Moventis Performance Material
Silwet® HAS604 from Moventis Performance Material
Silwet® 7280 from Moventis Performance Material
AgroSpred® 730 from Moventis Performance Material
Sylgard® 309 from Dow AgroScience Q2-5211 from Dow AgroScience
Tegopren® 5878
Maxx®
Du-Wett®
Designer®
Etc.

More preferably, the polysiloxane(s) can be selected from:

BREAK-THRU® S-240 from Evonik GmbH
BREAK-THRU® S-233 from Evonik GmbH (also known as Complement Super® or Etalfix Pro®)
BREAK-THRU® OE441 from Evonik GmbH
BREAK-THRU® OE444 from Evonik GmbH
BREAK-THRU® OE440 from Evonik GmbH
BREAK-THRU® S200 from Evonik GmbH
BREAK-THRU® S243 from Evonik GmbH
BREAK-THRU® S278 from Evonik GmbH
BREAK-THRU® S279 from Evonik GmbH Most preferably, the polysiloxane(s) can be selected from:

BREAK-THRU® S-240 from Evonik GmbH
BREAK-THRU® S-233 from Evonik GmbH (also known as Complement Super® or Etalfix Pro®)
BREAK-THRU® OE441 from Evonik GmbH
BREAK-THRU® S243 from Evonik GmbH These are adjuvants known as superspreaders, stickers, penetrants etc. However, none of these have ever been known to reduce the potentially phytotoxic effect of active ingredients. Particularly, since the increase of efficacy, would lead the skilled person to conclude that such adjuvants would only increase the phytotoxic risk.

Thus, the polysiloxanes according to the invention (in particular corresponding to Formula II) can achieve, at use concentrations of preferably from 0.0001 to 10% by volume, preferably from 0.001 to 5% by volume, and particularly preferably from 0.01 to 1% by volume (corresponding also to % by weight), reduced phytotoxicity, whilst at least maintaining the efficacy of the compounds according to the invention and keeping the tetramic acid compounds of formula (I) stable within the formulation.

Besides polysiloxanes, it has been found that rather surprisingly, adjuvants such as Geropon® DOS-PG and Trend®90 also provide formulations which have reduced phytotoxicity risks, but simultaenously improved efficacy on pests.

Geropon® DOS-PG from Rhodia is a Sodium dioctylsulphosuccinate (generally in glycol water solution).

Trend®90 from DuPont Solutions is a composition comprising Isodecyl alcohol ethoxylate.

However, most preferred are the polysiloxanes as described above as these provide surprisingly the best results for both phytotoxicity and efficacy.

Such tank-mix adjuvants can also be used with formulated active ingredients already comprising built-in adjuvants.

The Formulated Active Ingredients Prior to Tank-Mixing

In these "premix compositions" i.e. the compositions prior to tank-mixing with the tank-mix adjuvant according to the invention, the active ingredient is employed in pure form, a solid active ingredient for example in a specific particle size, or, preferably, together with—at least—one of the auxiliaries conventionally used in the art of formulation, such as extenders, solvents or surface-active compounds (surfactants). The compound according to formula (I) may be used as a suspension concentrate (SC), as an emulsion concentrate (EC), emulsion in water (EW), oil dispersion (OD), soluble liquid (SL) or as a solid formulation intended for dispersion or dilution (water dispersible granules (WG), wettable powder (WP), water soluble granules (SG), soluble powder (SP)). In one embodiments the compounds are applied as a dispersion, e.g. a dispersion of formulations such as a SC, WG or WP.

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues. Other possible carriers are materials made from carbohydrates, such as lactose or starch.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo¬lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propy¬lene glycol unit. Examples which may be mentioned are nonylphenoxypolyethoxyethanol, castor oil polyglycol ether, polypropylene glycol/polyethylene oxide adducts, tributylpheno¬xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl) ethyl¬ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the compositions are tris-(2-ethylhexyl)phosphate, tris-n-octyl phosphate and tris-butoxyethyl phosphate, where tris-(2-ethylhexyl)phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2ethylhexyl)-tripropylene-phosphonate, where bis-(2-ethylhexyl)-(n-octyl)-phosphonate is particularly preferred.

The compounds according to formula (I) can additionally be formulated to include a built-in adjuvant comprising an oil of vegetable or animal origin, a mineral oil, alkyl esters of such oils or mixtures of such oils and oil derivatives. The amount of built-in adjuvant is generally from 0.01 to 50%, based on the spray mixture. For example, the built-in adjuvant can be selected from mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. Preferred built-in adjuvant, are e.g. active components essentially 80% by weight alkyl esters of fish oils and 15% by weight methylated rapeseed oil, and also 5% by weight of customary emulsifiers and pH modifiers. Especially preferred built-in adjuvants comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other built-in adjuvants are also known from the Compendium of Herbicide Adjuvants, 5th Edition, Southern Illinois University, 2000.

The application and action of adjuvants can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

Furthermore, the addition of an organic solvent to the surfactant mixture can contribute to a further enhancement of action. Suitable solvents are, for example, Solvesso® (ESSO) and Aromatic Solvent® (Exxon Corporation).The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions it is also possible for formulations of alkylpyrrolidones, (e.g. Agrimax®) to be added to the spray mixture. Formulations of synthetic latices, such as, for example, polyacrylamide, polyvinyl compounds or poly-1 -p-menthene (e.g. Bond®, Courier® or Emerald®) can also be used. Solutions that contain propionic acid, for example Eurogkem Pen-e-trate®, can also be mixed into the spray mixture as activity-enhancing agents.

As a rule, the compositions prior to tankmixing with the tankmix adjuvant comprise 0.1 to 99%, especially 0.1 to 95% of active ingredient, and 5 to 99.9% of a surfactant (% in each case meaning percent by weight). Below are the contents of active ingredients, surfactant and where appropriate solvent of typical formulations of active ingredients.

Whereas concentrated premix compositions tend to be preferred for commercial goods, the end consumer as a rule uses dilute compositions (which are prepared by diluting the SC concentrates with solvents, both aqueous or non-aqueous) which have substantially lower concentrations of active ingredient. Preferred compositions are composed in particular as follows (%=percent by weight):

Suspension Concentrates:

active ingredient: 5 to 75%, preferably 10 to 50%, more preferably 10 to 40% water: 94 to 24%, preferably 88 to 30% surfactant: 1 to 40%, preferably 2 to 30%

Wettable Powders:

active ingredient: 0.5 to 90%, preferably 1 to 80%, more preferably 25 to 75% surfactant: 0.5 to 20%, preferably 1 to 15% solid carrier: 5 to 99%, preferably 15 to 98%

Wettable Granulates:

active ingredient: 0.5 to 30%, preferably 3 to 25%, more preferably 3 to 15% solid carrier: 99.5 to 70%, preferably 97 to 85%

Emulsifiable Concentrates:

active ingredient: 1 to 95%, preferably 5 to 50%, more preferably 5 to 20% surfactant: 1 to 30%, preferably 10 to 20% solvent: 5 to 98%, preferably 70 to 85%

Preferably, the term "active ingredient" refers to one of the tetramic acid compounds according to formula (I) , in particular formulas (i)-(v) and (i') to (v'). It also refers to mixtures of the compound of formula (I), in particular a compound selected from said (i)-(v) and (i') to (v'), with other insecticides, fungicides, herbicides, safeners, adjuvants and the like, which mixtures are specifically disclosed below.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO08/017388, which can enhance the efficacy of the inventive compounds; or other active ingredients for achieving specific effects, for example ammonium or phosphonium salts, in particular halides, (hydrogen)sulphates, nitrates, (hydrogen)carbonates, citrates, WO007/068427 and WO07/068428, which also can enhance the efficacy of the inventive compounds and which can be used in combination with penetration enhancers such as alkoxalated fatty acids; bactericides, fungicides, nematocides, plant activators, molluscicides or herbicides.

The application methods for the compositions, that is the methods of controlling pests of the abovementioned type, such as spraying, atomizing, dressing, scattering or pouring—which are to be selected to suit the intended aims of the prevailing circumstances—and the use of the compositions for controlling pests of the abovementioned type are also subject of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question.

In order to apply a compound of formula I as an insecticide, acaricide, nematicide or molluscicide to a pest, a locus of pest, or to a plant susceptible to attack by a pest, a compound of formula I is usually formulated into a composition which includes, in addition to the compound of formula I, a suitable inert diluent or carrier. The formulated composition is then tank-mixed with the tank-mix adjuvant of the invention, preferably a polysiloxane, more preferably a polysiloxane according to formula (II) prior to treatment of the crop.

It is preferred that all compositions (both solid and liquid formulations) comprise, by weight, 0.0001 to 95%, more preferably 1 to 85%, for example 5 to 60%, of a compound of formula I. The composition is generally used for the control of pests such that a compound of formula I is applied at a rate of from 0.1 g to 10 kg per hectare, preferably from 1 g to 6 kg per hectare, more preferably from 1 g to 1 kg per hectare.

In another aspect the present invention provides an insecticidal, acaricidal, nematicidal or molluscicidal composition comprising an insecticidally, acaricidally, nematicidally or molluscicidally effective amount of a compound of formula I, the tank-mix adjuvant according to the invention (e.g. a polysiloxane, preferably according to formula (II)) and a suitable carrier or diluent therefor.

In a still further aspect the invention provides a method of combating and controlling pests at a locus which comprises treating the pests or the locus of the pests with an insecticidally, acaricidally, nematicidally or molluscicidally effective amount of a composition comprising a compound of formula I and one or more tank-mix adjuvants, preferably polysiloxane, more preferably polysiloxane according to formula (II).

The compositions can be chosen from a number of formulation types, which are then dispersed or diluted and mixed with the polysiloxane tank-mix adjuvant prior to application on the field e.g. soluble powders (SP), water soluble granules (SG), water dispersible granules (WG), wettable powders (WP), emulsifiable concentrates (EC), dispersible concentrates (DC), and suspension concentrates (SC).

Soluble powders (SP) may be prepared by mixing a compound of formula I with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Dispersible Concentrates (DC) may be prepared by dissolving a compound of formula I in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula I in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

Oil-based suspension concentrate (OD) may be prepared similarly by suspending finely divided insoluble solid particles of a compound of formula I in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, anti-oxidants, dyestuffs, and/or inert filler materials. An OD is intended and suitable for dilution with water before use to produce a spray solution with sufficient stability to allow spray application through appropriate equipment.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention. Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

A composition of the present invention may include one or more additives to improve the performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthaleve sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula I may be applied by any of the known means of applying pesticidal compounds. For example, it may formulated as an SC, EC, WG, WP, SG, SP, SL, OD, EW diluted and mixed with the polysiloxane tank-mix adjuvant and then applied, to the pests or to a locus of the pests (such as a habitat of the pests, or a growing plant liable to infestation by the pests) or to any part of the plant, including the foliage, stems, branches or roots, directly or it may be sprayed on, applied by dipping, applied as a vapour or applied through distribution or incorporation of a composition (such as a composition packed in a water-soluble bag) in soil or an aqueous environment.

A compound of formula I may also be injected into plants or sprayed onto vegetation using electrodynamic spraying techniques or other low volume methods.

Compositions for use as aqueous preparations (aqueous solutions or dispersions) are generally supplied in the form of a concentrate containing a high proportion of the active ingredient, the concentrate being added to water before use. These concentrates in the present invention are either an SC, SC, EC, WG, WP, SG or SP, SL, OD, EW which often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

Further Active Ingredients

The composition or combination pack of the invention can comprise other than the tetramic acid compound according to formula (I) can further include additional active ingredients. Other active ingredients can include acaricides (AC), algicides (AL), attractants (AT), repellents (RE), bactericides (BA), fungicides (FU), herbicides (HE), insecticides (IN), agents to combat snails and slugs (molluscicides, MO), nematicides (NE), rodenticides (RO), sterilants (ST), viricides (VI), growth regulators (PG), plant strengthening agents (PS), micronutrients (MI) and macronutrients (MA).

Preferred pesticides are HB, FU, IN, PG, MI and particularly HB, FU, IN.

Some active ingredients or active organisms are listed, for example, in "The Pesticide Manual", 14th edition, 2006, The British Crop Protection Council, or in "The Manual of Biocontrol Agents", 2004, The British Crop Protection Council.

The present application, however, is not limited to these active ingredients listed therein, but also includes more modern active ingredients not yet cited in the aforementioned monograph.

The group of herbicides includes, by way of example but not limited to these, products with the following active ingredients or active ingredient mixtures: acetochlor, acifluorfen, aclonifen, acrolein, alachlor, ametryne, amitrole, asulam, atrazine, benazolin, bensulfuronmethyl, bentazon, benzofenap, bialaphos, bifenox, bromacil, bromobutide, bromofenoxim, bromoxynil, butachlor, butafenacil, chlomethoxyfen, chloramben, chloroacetic acid, chlorbromuron, chlorimuron-ethyl, chlorotoluron, chlomitrofen, chlorotoluron, chlorthaldimethyl, clomazone, clodinafop, clopyralid, clomeprop, cyanazine, 2,4-D, 2,4-DB, dimuron, dalapon, desmedipham, desmetryn, dicamba, dichlobenil, dichloroprop, diclofop, difenzoquat, diflufenican, dimefuron, dimethachlor, dimethametryn, dimethenamid, dinitramine, diquat, diuron, endothall, ethametsulphuron-methyl, ethofumesan, fenac, fenclorim, fenoxaprop, fenoxaprop-ethyl, flamprop-methyl, flazasulfuron, fluazifop, fluazifop-p-butyl, flumetsulam, flumiclorac-penyl, fluoroglycofen, flumetsulam, flumeturon, flumioxazin, flupoxam, flupyrsulfuron, flupropanate, fluridone, fluoroxypyr, flurtamone, fomasafen, fosamine, glufosinate, glyphosate and its salts, (for example alkylammonium or alkali metal salts), haloxyfop, imazameth, imazamethabenz, imazamox, imazapic, imazapyr, imazaquin, imazethapyr, iodosulfuron, ioxynil, isoproturon, isoxaben, isoxapyrifop, lactofen, lenacil, linuron, MCPA, MCPB, mecoprop, mefenacet, mesotrione, metazachlor, methabenzthiazuron, metalachlor, methylarsenic acid, metolachlor, metobenzuron, metosulam, mesosulfuron, metamitron, metsulfuron, naproanilide, naptalam, neburon, nicosulfuron, nonanoic acid, norflurazon, oryzalin, oxadiazon, oxyfluorfen, paraquat, pendimethalin, phenmedipham, picloram, picolinafen, pretilachlor, prodiamine, prometon, prometryn, propachlor, propazine, propisochlor, propyzamide, pyrazolynate, pyrazosulfuron-ethyl, pyributicarb, pyridat, quinclorac, quizalofop-ethyl, quizalofop-P, quinclorac, rimsulfuron, siduron, simazine, simetryn, sulphamic acid, sulphonylurea, 2,3,6-TBA, terbumeton, terbuthylazine, terbutryn, trichloroacetic acid, triclopyr, trietazine, thenylchlor, thiazopyr, tralkoxydim, trifuralin, tritosulfuron, and salts thereof and mixtures thereof.

In another embodiment of the invention, the herbicides are aryloxyphenoxypropionic herbicides which includes chlorazifop, clodinafop, clofop, cyhalofop, diclofop, fenoxaprop, fenoxaprop-P, fenthiaprop, fluziafop, fluziafop-P, haloxyfop, haloxyfop-P, isoxapyrifop, metamifop, propaquizafop, quizalofop, quizalofop-P, trifop, and salts thereof and mixtures thereof.

Examples of active fungicide active ingredients which are combined in crop protection composition products alone or in a mixture with other active ingredients are: azoxystrobin, benalaxyl, benomyl, bitertanol, borax, bromocuonazole, sec-butylamine, captafol, captan, calcium polysulphide, carbendazim, quinomethionate, chlorothalonil, chlozolinate, copper and its derivatives, copper sulphate, cyprodinil, cyproconazole, dichlofluanid, dichlorophen, diclomezine, dicloran, diethofencarb, difenoconazole, dimethomorph, diniconazole, dithianon, epoxiconazole, famoxadone, fenarimol, fenbuconazole, fenfuram, fenhexamid, fenpiclonil, fenpropidin, fenpropimorph, fentin, fluazinam, fludioxonil, fluoroimide, fluquinconazole, flusulfamide, flutolanil, folpet, fosetyl, furalaxyl, guazatine, hexachlorobenzene, hexaconazole, hydroxyquinoline sulphate, imibenconazole, iminoctadine, ipconazole, iprodione, kasugamycin, kresoximmethyl, mancozeb, maneb, mefenoxam, mepanipyrim, mepronil, mercury chloride, metam, metalaxyl, metconazole, metiram, nabam, nickel bis(dimethyldithiocarbamate), nuarimol, oxadixil, oxine-copper, oxolinic acid, penconazole, pencycuron, picoxystrobin, phthalide, polyoxin B, prochloraz, procymidone, propamocarb, propiconazole, propineb, pyrifenox, pyraclostrobin, pyroquilon, quintozene, spiroxamine, sulphur, tebuconazole, tecloftalam, tecnazene, thiabendazole, thifluzamide, thiophanate-methyl, thiram, tolclofos-methyl, tolylfluanid, triadimefon, triadimenol, triazoxide, trifloxystrobin, triforin, triticonazole, vinclozolin, zineb, ziram, salts thereof and mixtures thereof.

In another embodiment of the invention, the fungicides are strobilurin and related fungicides classes of chemistries which include azoxystrobin, enestrobin, picoxystrobin, pyraclostrobin, kresoxim-methyl, trifloxystrobin, dimoxystrobin, metominostrobin, orysastrobin, famoxadone, fluoxastrobin, fenamidone, pyribencarb, cyazofamid, amisulbrom, and mixtures thereof; these fungicides and mixtures thereof are used in cereals (wheat, barley, rye, triticale, rice) to control crop diseases.

Examples of active ingredients (alone or in mixtures) of insecticides are: abamectin, acephate, acetamiprid, acrinathrin, amitraz, azadirachtin, azamethiphos, azinphos-methyl, azocyclotin, bensultap, bifenthrin, bromopropylate, buprofezin, butoxycarboxim, cartap, chlorfenapyr, chlorfenson, chlorfluazuron, clofentezine, coumaphos, cyfluthrin, beta-cyfluthrin, lambda-cyhalothrin, cypermethrin, alpha-cypermethrin, theta-cypermethrin, cyromazine, DDT, deltamethrin, diafenthiuron, dicofol, dicrotophos, difenthiuron, diflubenzuron, dimethoate, emamectin benzoate, endosulfan, esfenvalerate, etoxazole, fenazaquin, fenbutatin oxide, fenoxycarb, fenpyroximate, fipronil, fluazuron, flucycloxuron, flufenoxuron, tau-fluvalinate, formetanate, furathiocarb, halofenozide, gamma-HCH, hexaflumuron, hexythiazox, hydramethylnon, hydrogen cyanide, imidacloprid, lufenuron, methamidophos, methidathion, methiocarb, methomyl, methoxychlor, mevinphos, milbemectin, mineral oils, monocrotophos, nicotin, nitenpyram, novaluron, omethoate, organophosphorus compounds, oxamyl, oxydemeton-methyl, pentachlorophenol, phosphamidon, pymetrozin, permethrin, profenofos, pyridaben, rapeseed oil, resmethrin, rotenone, spinosad, sulfluramid, tebufenozide, tebufenpyrad, tebupirimfos, teflubenzuron, tetrachlorvinphos, tetradifon, tetramethrin, thiamethoxam, thiocyclam, thiodicarb, tralomethrin, trichlorfon, friflumuron, trimethacarb, vamidothion, and salts thereof and mixtures thereof.

Examples of active ingredients in products from the group of growth regulators are: 6-benzylaminopurine, chlormequat, chlorphonium, cimectacarb, clofencet, cloxyfonac, cyanamide, cyclanilide, daminozide, dikegulac, ethephon, flumetralin, forchlorfenuron, gibberilic acid, inabenfide, indolylbutyronic acid, 2-(1-naphthyl)acetamide, mepiquat, paclobutrazol, N-phenyl-phthalaminic acid, thidiazuron, trinexapac-ethyluniconzole, and salts thereof and mixtures thereof.

The mixing partners of the compound of formula I may also be in the form of esters or salts, as mentioned e.g. in The Pesticide Manual, 12th Edition (BCPC), 2000.

Further mixture partners for the compounds of this invention according to formula (I) are mentioned in the following applications: WO2009/049851, WO2010/066780, WO2010/063670 and are incorporated herein by reference. Particularly preferred mixture partners are cited in PCT/EP2012/073890, PCT/EP2013/050790, PCT/EP2013/050792, PCT/EP2013/050793 and PCT/EP2013/050794 and are also incorporated herein by reference.

Plant nutrients and plant micronutrients which are applied in liquid form in liquid preparation in highly diverse forms alone or in combination with other nutrients or in combination with crop protection compositions are for example nitrogen (in nitrogen fertilizers), phosphate, potassium, calcium, magnesium, manganese, boron, copper, iron (in iron fertilizers), selenium, cobalt, zinc, which can also be present, for example, as oxides, sulphates or carbonates, and others which are known under the name micronutrients.

When applied to the useful plants the compound of formula (I) is generally applied at a rate of 1 to 1000 g a.i./ha and with optionally 1 to 2000 g a.i./ha, of a second active ingredient, depending on the chemical class of said second active ingredient. Preferably, when applied to the useful plants the compound of formula (I) is generally applied at a rate of 1 to 500 g a.i./ha and with optionally 1 to 1000 g a.i./ha, of a second active ingredient, depending on the chemical class of said second active ingredient. More preferably, when applied to the useful plants the compound of formula (I) is generally applied at a rate of 1 to 250 g a.i./ha and with optionally 1 to 500 g a.i./ha, of a second active ingredient, depending on the chemical class of said second active ingredient.

Uses

The combination pack refers to a comprising a combination of a compound according to formula (I) and an adjuvant selected from one or more polysiloxanes, wherein a first container contains the tetramic acid compound according to formula (I) and a second container contains the adjuvant selected from one or more polysiloxanes. The tetramic acid compound according to formula (I) from the first container and the polysiloxane adjuvant are mixed together prior to the application onto the crops.

The composition refers to the already diluted formulated tetramic acid compound mixed with the polysiloxane adjuvant, ready for application on the crops.

The composition and combination pack according to the invention can be used on a number of plants to target a number of different pests.

The present invention also relates to a method of controlling insects, acarines, nematodes or molluscs which comprises applying to a pest, to a locus of a pest, or to a plant susceptible to attack by a pest a combination of compounds of formula (I) and polysiloxane (e.g. according to formula (II)); seeds comprising a mixture of compounds of formula (I) and polysiloxane (e.g. according to formula (II)); and a method comprising coating a seed with a mixture of compounds of formula (I) and polysiloxane (e.g. according to formula (II)). Compounds of formula (I) and polysiloxane (e.g. according to formula (II)) may be provided and/or used in amounts such that they are capable of efficient pest control without causing phytoxicity on the plants. For example, the present invention includes pesticidal mixtures comprising a compound of formula (I) and one or more polysiloxanes in relative amounts sufficient for increasing the efficacy of formula (I) alone and the phytotoxicity of the compound;

agricultural compositions comprising a mixture of a compound of formula (I) and polysiloxane (e.g. according to formula (II)) in relative amounts sufficient for increasing the efficacy of formula (I) alone and the phytotoxicity of the compound; the use of a mixture of compounds of formula (I) and polysiloxane (e.g. according to formula (II)) in effective amounts for combating animal pests; a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a mixture of compounds of formula (I) and polysiloxane (e.g. according to formula (II)) in a an effective amount; a method for protecting crops from attack or infestation by animal pests which comprises contacting a crop with a mixture of compounds of formula (I) and polysiloxane (e.g. according to formula (II)) in an effective amount; a method for the protection of seeds from soil insects and of the seedlings' roots and shoots from soil and foliar insects comprising contacting the seeds before sowing and/or after pre-germination with a mixture of compounds of formula (I) and polysiloxane (e.g. according to formula (II)) in an effective amount; a method of controlling insects, acarines, nematodes or molluscs which comprises applying to a pest, to a locus of a pest, or to a plant susceptible to attack by a pest a combination of compounds of formula (I) and polysiloxane (e.g. according to formula (II)) in an effective amount. Mixtures of A and B will normally be applied in an insecticidally, acaricidally, nematicidally or molluscicidally effective amount. In application compounds of formula (I) and polysiloxane (e.g. according to formula (II)) may be applied simultaneously or separately.

The mixtures of the present invention can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are herein collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The mixtures of the invention are particularly effective against insects, acarines and/or nematodes.

According to the invention "useful plants" with which the mixture according to the invention can be applied, typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ACCase inhibitors, ALS inhibitors, for example primisulfuron, prosulfuron and trifloxysulfuron, EPSPS (5-enol-pyrovyl-shikimate-3-phosphatesynthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins, for example insecticidal proteins from Bacillus cereus or Bacillus popilliae; or insecticidal proteins from Bacillus thuringiensis, such as δ-endotoxins, e.g. Cry1Ab, Cry1Ac, Cry1F, Cry1Fa2, Cry2Ab, Cry3A, Cry3Bb1 or Cry9c, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases. In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). An example for a truncated toxin is a truncated Cry1Ab, which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera). Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9c toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCOT® (cotton variety that expresses a Vip3A and a Cry1Ab toxin); NewLeaf® (potato variety that expresses a Cry3A toxin); NatureGard® and Protecta®. Further examples of such transgenic crops are:

1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from Agrobacterium sp. strain CP4, which imparts tolerance to the herbicide Roundup® (contains glyphosate), and also a Cry1Ab toxin obtained from Bacillus thuringiensis subsp. kurstaki which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906). Useful plants of elevated interest in connection with present invention are cereals; soybean; corn; cotton; rice; oil seed rape; sunflowers; sugarcane; pome fruits; stone fruits; citrus fruits; peanuts, potatoes; coffee; tea; strawberries; turf; vines and vegetables, such as tomatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds. Insecticides that are of particular interest for treating seeds include thiamethoxam, imidacloprid and clothianidin.

A further aspect of the instant invention is a method of protecting natural substances of plant and/or animal origin, which have been taken from the natural life cycle, and/or their processed forms against attack of pests, which comprises applying to said natural substances of plant and/or animal origin or their processed forms a combination of compounds of formula (I) and polysiloxane (e.g. according to formula (II)) in an effective amount.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

A preferred embodiment is a method of protecting natural substances of plant origin, which have been taken from the natural life cycle, and/or their processed forms against attack of pests, which comprises applying to said natural substances of plant and/or animal origin or their processed forms a combination of compounds of formula (I) and polysiloxane (e.g. according to formula (II)) in an amount effective to increase efficacy and reduce the phytotoxicity of compounds according to formula (I).

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of compounds of formula (I) and polysiloxane (e.g. according to formula (II)) in an effective amount.

The composition and combination packs according to the present invention are furthermore particularly effective against the following pests: Myzus persicae (aphid), Aphis gossypii (aphid), Aphis fabae (aphid), Lygus spp. (capsids), Dysdercus spp. (capsids), Nilaparvata lugens (planthopper), Nephotettixc incticeps (leafhopper), Nezara spp. (stinkbugs), Euschistus spp. (stinkbugs), Leptocorisa spp. (stinkbugs), Frankliniella occidentalis (thrip), Thrips spp. (thrips), Leptinotarsa decemlineata (Colorado potato beetle), Anthonomus grandis (boll weevil), Aonidiella spp. (scale insects), Trialeurodes spp. (white flies), Bemisia tabaci (white fly), Ostrinia nubilalis (European corn borer), Spodoptera littoralis (cotton leafworm), Heliothis virescens (tobacco budworm), Helicoverpa armigera (cotton bollworm), Helicoverpa zea (cotton bollworm), Sylepta derogata (cotton leaf roller), Pieris brassicae (white butterfly), Plutella xylostella (diamond back moth), Agrotis spp. (cutworms), Chilo suppressalis (rice stem borer), Locusta migratoria (locust), Chortiocetes terminifera (locust), Diabrotica spp. (rootworms), Panonychus ulmi (European red mite), Panonychus citri (citrus red mite), Tetranychus urticae (two-spotted spider mite), Tetranychus cinnabarinus (carmine spider mite), Phyllocoptruta oleivora (citrus rust mite), Polyphagotarsonemus latus (broad mite), Brevipalpus spp. (flat mites), Boophilus microplus (cattle tick), Dermacentor variabilis (American dog tick), Ctenocephalides fees (cat flea), Liriomyza spp. (leafminer), Musca domestica (housefly), Aedes aegypti (mosquito), Anopheles spp. (mosquitoes), Culex spp. (mosquitoes), Lucillia spp. (blowflies), Blattella germanica (cockroach), Periplaneta americana (cockroach), Blatta orientalis (cockroach), termites of the Mastotermitidae (for example Mastotermes spp.), the Kalotermitidae (for example Neotermes spp.), the Rhinotermitidae (for example Coptotermes formosanus, Reticulitermes flavipes, R. speratu, R. virginicus, R. hesperus, and R. santonensis) and the Termitidae (for example Globitermes sulfureus), Solenopsis geminata (fire ant), Monomorium pharaonis (pharaoh's ant), Damalinia spp. and Linognathus spp. (biting and sucking lice), Meloidogyne spp. (root knot nematodes), Globodera spp. and Heterodera spp. (cyst nematodes), Pratylenchus spp. (lesion nematodes), Rhodopholus spp. (banana burrowing nematodes), Tylenchulus spp.(citrus nematodes), Haemonchus contortus (barber pole worm), Caenorhabditis elegans (vinegar eelworm), Trichostrongylus spp. (gastro intestinal nematodes) and Deroceras reticulatum (slug), Diaphorina spp (psyllids), Cacopsylla spp (psyllids), and Paratrioza or Bacteriocera (psyllids)

In another embodiment, the composition and combination packs according to the present invention are also particularly effective against the following pests: from the order Acarina, for example, Acalitus spp, Aculus spp, Acaricalus spp, Aceria spp, Acarus siro, Amblyomma spp., Argas spp., Boophilus spp., Brevipalpus spp., Bryobia spp, Calipitrimerus spp., Chorioptes spp., Dermanyssus gallinae, Dermatophagoides spp, Eotetranychus spp, Eriophyes spp., Hemitarsonemus spp, Hyalomma spp., Ixodes spp., Olygonychus spp, Ornithodoros spp., Polyphagotarsone latus, Panonychus spp., Phyllocoptruta oleivora, Phytonemus spp, Polyphagotarsonemus spp, Psoroptes spp., Rhipicephalus spp., Rhizoglyphus spp., Sarcoptes spp., Steneotarsonemus spp, Tarsonemus spp. and Tetranychus spp.;

from the order Anoplura, for example,

Haematopinus spp., Linognathus spp., Pediculus spp., Pemphigus spp. and Phylloxera spp.;

from the order Coleoptera, for example,

Agriotes spp., Amphimallon majale, Anomala orientalis, Anthonomus spp., Aphodius spp, Astylus atromaculatus, Ataenius spp, Atomaria linearis, Chaetocnema tibialis, Cerotoma spp, Conoderus spp, Cosmopolites spp., Cotinis nitida, Curculio spp., Cyclocephala spp, Dermestes spp., Diabrotica spp., Diloboderus abderus, Epilachna spp., Eremnus spp., Heteronychus arator, Hypothenemus hampei, Lagria vilosa, Leptinotarsa decemLineata, Lissorhoptrus spp., Liogenys spp, Maecolaspis spp, Maladera castanea, Megascelis spp, Melighetes aeneus, Melolontha spp., Myochrous armatus, Orycaephilus spp., Otiorhynchus spp., Phyllophaga spp, Phlyctinus spp., Popillia spp., Psylliodes spp., Rhyssomatus aubtilis, Rhizopertha spp., Scarabeidae, Sitophilus spp., Sitotroga spp., Somaticus spp, Sphenophorus spp, Sternechus subsignatus, Tenebrio spp., Tribolium spp. and Trogoderma spp.;

from the order Diptera, for example,

Aedes spp., Anopheles spp, Antherigona soccata, Bactrocea oleae, Bibio hortulanus, Bradysia spp, Calliphora erythrocephala, Ceratitis spp., Chrysomyia spp., Culex spp., Cuterebra spp., Dacus spp., Delia spp, Drosophila melanogaster, Fannia spp., Gastrophilus spp., Geomyza tripunctata, Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis spp, Rivelia quadrifasciata, Scatella spp, Sciara spp., Stomoxys spp., Tabanus spp., Tannia spp. and lipula spp.;

from the order Hemiptera, for example,

Acanthocoris scabrator, Acrosternum spp, Adelphocoris lineolatus, Amblypelta nitida, Bathycoelia thalassina, Blissus spp, Cimex spp., Clavigralla tomentosicollis, Creontiades spp, Distantiella theobroma, Dichelops furcatus, Dysdercus spp., Edessa spp, Euchistus spp., Eurydema pulchrum, Eurygaster spp., Halyomorpha halys, Horcias nobilellus, Leptocorisa spp., Lygus spp, Margarodes spp, Murgantia histrionic, Neomegalotomus spp, Nesidiocoris tenuis, Nezara spp., Nysius simulans, Oebalus insularis, Piesma spp., Piezodorus spp, Rhodnius spp., Sahlbergella singularis, Scaptocoris castanea, Scotinophara spp., Thyanta spp, Triatoma spp., Vatiga illudens;

Acyrthosium pisum, Adalges spp, Agalliana ensigera, Agonoscena targionii, Aleurodicus spp, Aleurocanthus spp, Aleurolobus barodensis, Aleurothrixus floccosus, Aleyrodes brassicae, Amarasca biguttula, Amritodus atkinsoni, Aonidiella spp., Aphididae, Aphis spp., Aspidiotus spp., Aulacorthum solani, Bactericera cockerelli, Bemisia spp, Brachycaudus spp, Brevicoryne brassicae, Cacopsylla spp, Cavariella aegopodii Scop., Ceroplaster spp., Chrysomphalus aonidium, Chrysomphalus dictyospermi, Cicadella spp, Cofana spectra, Cryptomyzus spp, Cicadulina spp, Coccus hesperidum, Dalbulus maidis, Dialeurodes spp, Diaphorina citri, Diuraphis noxia, Dysaphis spp, Empoasca spp., Eriosoma larigerum, Erythroneura spp., Gascardia spp., Glycaspis brimblecombei, Hyadaphis pseudobrassicae, Hyalopterus spp, Hyperomyzus pallidus, Idioscopus clypealis, Jacobiasca lybica, Laodelphax spp., Lecanium corni, Lepidosaphes spp., Lopaphis erysimi, Lyogenys maidis, Macrosiphum spp., Mahanarva spp, Metcalfa pruinosa, Metopolophium dirhodum, Myndus crudus, Myzus spp., Neotoxoptera sp, Nephotettix spp., Nilaparvata spp., Nippolachnus piri Mats, Odonaspis ruthae, Oregma lanigera Zehnter, Parabemisia myricae, Paratrioza cockerelli, Parlatoria spp., Pemphigus spp., Peregrinus maidis, Perkinsiella spp, Phorodon humuli, Phylloxera spp, Planococcus spp., Pseudaulacaspis spp., Pseudococcus spp., Pseudatomoscelis seriatus, Psylla spp., Pulvinaria aethiopica, Quadraspidiotus spp., Quesada gigas, Recilia dorsalis, Rhopalosiphum spp., Saissetia spp., Scaphoideus spp., Schizaphis spp., Sitobion spp., Sogatella furcifera, Spissistilus festinus, Tarophagus Proserpina, Toxoptera spp, Trialeurodes spp, Tridiscus sporoboli, Trionymus spp, Trioza erytreae, Unaspis citri, Zygina flammigera, Zyginidia scutellaris;

from the order Hymenoptera, for example,

Acromyrmex, Arge spp, Atta spp., Cephus spp., Diprion spp., Diprionidae, Gilpinia polytoma, Hoplocampa spp., Lasius spp., Monomorium pharaonis, Neodiprion spp., Pogonomyrmex spp, Slenopsis invicta, Solenopsis spp. and Vespa spp.;

from the order Isoptera, for example,

Coptotermes spp, Corniternes cumulans, Incisitermes spp, Macrotermes spp, Mastotermes spp, Microtermes spp, Reticulitermes spp.; Solenopsis geminate from the order Lepidoptera, for example, Acleris spp., Adoxophyes spp., Aegeria spp., Agrotis spp., Alabama argillaceae, Amylois spp., Anticarsia gemmatalis, Archips spp., Argyresthia spp, Argyrotaenia spp., Autographa spp., Bucculatrix thurberiella, Busseola fusca, Cadra cautella, Carposina nipponensis, Chilo spp., Choristoneura spp., Chrysoteuchia topiaria, Clysia ambiguella, Cnaphalocrocis spp., Cnephasia spp., Cochylis spp., Coleophora spp., Colias lesbia, Cosmophila flava, Crambus spp, Crocidolomia binotalis, Cryptophlebia leucotreta, Cydalima perspectalis, Cydia spp., Diaphania perspectalis, Diatraea spp., Diparopsis castanea, Earias spp., Eldana saccharina, Ephestia spp., Epinotia spp, Estigmene acrea, Etiella zinckinella, Eucosma spp., Eupoecilia ambiguella, Euproctis spp., Euxoa spp., Feltia jaculiferia, Grapholita spp., Hedya nubiferana, Heliothis spp., Hellula undalis, Herpetogramma spp, Hyphantria cunea, Keiferia lycopersicella, Lasmopalpus lignosellus, Leucoptera scitella, Lithocollethis spp., Lobesia botrana, Loxostege bifidalis, Lymantria spp., Lyonetia spp., Malacosoma spp., Mamestra brassicae, Manduca sexta, Mythimna spp, Noctua spp, Operophtera spp., Orniodes indica, Ostrinia nubilalis, Pammene spp., Pandemis spp., Panolisflammea, Papaipema nebris, Pectinophora gossypiela, Perileucoptera cojfeella, Pseudaletia unipuncta, Phthorimaea operculella, Pieris rapae, Pieris spp., Plutella xylostella, Prays spp., Pseudoplusia spp, Rachiplusia nu, Richia albicosta, Scirpophaga spp., Sesamia spp., Sparganothis spp., Spodoptera spp., Sylepta derogate, Synanthedon spp., Thaumetopoea spp., Tortrix spp., Trichoplusia ni, Tuta absoluta, and Yponomeuta spp.;

from the order Mallophaga, for example,

Damalinea spp. and Trichodectes spp.;

from the order Orthoptera, for example,

Blatta spp., Blattella spp., Gryllotalpa spp., Leucophaea maderae, Locusta spp., Neocurtilla hexadactyla, Periplaneta spp., Scapteriscus spp, and Schistocerca spp.;

from the order Psocoptera, for example,

Liposcelis spp.;

from the order Siphonaptera, for example,

Ceratophyllus spp., Ctenocephalides spp. and Xenopsylla cheopis;

from the order Thysanoptera, for example,

Calliothrips phaseoli, Frankliniella spp., Heliothrips spp, Hercinothrips spp., Parthenothrips spp, Scirtothrips aurantii, Sericothrips variabilis, Taeniothrips spp., Thrips spp;

from the order Thysanura, for example,

Lepisma saccharina.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

The mixtures of the invention may be used for pest control on various plants, including soybean, alfalfa, brassicas (e.g. broccoli, cabbage, cauliflower), or oil crops, such as oilseed rape, mustard, canola, poppies, olives, sunflowers, coconut, castor, cocoa or ground nuts, or potatoes (including sweet potatoes), almonds, fruiting vegetables (e.g. tomatoes, pepper, chili,eggplant, etc.), leafy vegetables (lettuce, spinach), bulb vegetables (e.g. onion, leek etc.), grapes, fruit, for instance pomaceous fruit, stone fruit or soft fruit (e.g. apples, pears, plums, peaches, nectarines, almonds, cherries etc.) or berries, for example strawberries, raspberries or blackberries.

Other suitable target crops are, in particular, cereals, such as wheat, barley, rye, oats, rice, maize or sorghum; beet, such as sugar or fodder beet; leguminous crops, such as beans, lentils, peas, peanuts or soya; cucurbits, such as pumpkins, cucumbers, squash or melons; fibre plants, such as cotton, flax, hemp or jute; citrus fruit, such as oranges, lemons, grapefruit or tangerines; vegetables, such as spinach, lettuce, asparagus, cabbages, carrots, onions, or bell peppers; Lauraceae, such as avocado, Cinnamonium or camphor; and also tobacco, nuts (e.g. pecan nuts, walnut), coffee, sugarcane, tea, pepper, grapevines, tropical fruits (e.g. papaya, mango), hops, the plantain family, latex plants and ornamentals. The mixtures of the invention can also be applied on turf, lawn and pastures.

The mixtures of the invention may be used on soybean to control, for example, Elasmopalpus lignosellus, Diloboderus abderus, Diabrotica speciosa, Sternechus subsignatus, Formicidae, Agrotis ypsilon, Julus sspp., Anticarsia gemmatalis, Megascelis ssp., Procornitermes ssp., Gryllotalpidae, Nezara viridula, Piezodorus spp., Acrosternum spp., Neomegalotomus spp., Cerotoma trifurcata, Popillia japonica, Edessa spp., Liogenys fuscus, Euchistus heros, stalk borer Scaptocoris castanea, phyllophaga spp., Pseudoplusia includens, Spodoptera spp., Bemisia tabaci, Agriotes spp. Aphis sp (e.g. Aphis glycines). The mixtures of the invention are preferably used on soybean to control Diloboderus abderus, Diabrotica speciosa, Nezara viridula, Piezodorus spp., Acrosternum spp., Cerotoma trifurcata, Popillia japonica, Euchistus heros, phyllophaga spp., Agriotes sp, Aphis sp.

The mixtures of the invention may be used on corn to control, for example, Euchistus heros, Dichelops furcatus, Diloboderus abderus, Elasmopalpus lignosellus, Spodoptera frugiperda, Nezara viridula, Cerotoma trifurcata, Popillia japonica, Agrotis ypsilon, Diabrotica speciosa, Heteroptera, Procornitermes ssp., Scaptocoris castanea, Formicidae, Julus ssp., Dalbulus maidis, Diabrotica virgifera, Mocis latipes, Bemisia tabaci, heliothis spp., Tetranychus spp., thrips spp., phyllophaga spp., scaptocoris spp., Liogenys fuscus, Spodoptera spp., Ostrinia spp., Sesamia spp., Agriotes spp., Aphis sp. The mixtures of the invention are preferably used on corn to control Euchistus heros, Dichelops furcatus, Diloboderus abderus, Nezara viridula, Cerotoma trifurcata, Popillia japonica, Diabrotica speciosa, Diabrotica virgifera, Tetranychus spp., thrips spp., phyllophaga spp., scaptocoris spp., Agriotes spp., Aphis sp The mixtures of the invention may be used on sugar cane to control, for example, Sphenophorus spp., termites, Mahanarva spp. The mixtures of the invention are preferably used on sugar cane to control termites, Mahanarva spp.

The mixtures of the invention may be used on alfalfa to control, for example, Hypera brunneipennis, Hypera postica, Collas eurytheme, Collops spp., Empoasca solana, Epitrix, Geocoris spp., Lygus hesperus, Lygus lineolaris, Spissistilus spp., Spodoptera spp., Trichoplusia ni. The mixtures of the invention are preferably used on alfalfa to control Hypera brunneipennis, Hypera postica, Empoasca solana, Epitrix, Lygus hesperus, Lygus lineolaris, Trichoplusia ni.

The mixtures of the invention may be used on brassicas to control, for example, Plutella xylostella, Pieris spp., Mamestra spp., Plusia spp., Trichoplusia ni, Phyllotreta spp., Spodoptera spp., Empoasca solana, thrips spp., Spodoptera spp., Delia spp. Brevicoryne sp, Macrosiphum sp. The mixtures of the invention are preferably used on brassicas to control Plutella xylostella Pieris spp., Plusia spp., Trichoplusia ni, Phyllotreta spp., thrips sp The mixtures of the invention may be used on oil seed rape, e.g. canola, to control, for example, Meligethes spp., Ceutorhynchus napi, Psylloides spp.

The mixtures of the invention may be used on potatoes, including sweet potatoes, to control, for example, Empoasca spp., Leptinotarsa spp., Diabrotica speciosa, Phthorimaea spp., Paratrioza spp., Maladera matrida, Agriotes spp., Bemisia sp, Myzus sp., Macrosiphum sp. Aphis sp, Aulacorthum sp. Rhopalosiphum sp. The mixtures of the invention are preferably used on potatoes, including sweet potatoes, to control Empoasca spp., Leptinotarsa spp., Diabrotica speciosa, Phthorimaea spp., Paratrioza spp., Agriotes spp, Bemisia sp, Myzus sp., Macrosiphum sp. Aphis sp, Aulacorthum sp. Rhopalosiphum sp.

The mixtures of the invention may be used on cotton to control, for example, Aphis gossypii, Anthonomus grandis, Pectinophora spp., heliothis spp., Spodoptera spp., Tetranychus spp., Empoasca spp., thrips spp., Bemisia tabaci, Lygus spp., phyllophaga spp., Scaptocoris spp. The mixtures of the invention are preferably used on cotton to control Aphis gossypii, Anthonomus grandis, Tetranychus spp., Empoasca spp., thrips spp., Lygus spp., phyllophaga spp., Scaptocoris spp.

The mixtures of the invention may be used on rice to control, for example, Nilaparvata lugens, Leptocorisa spp., Cnaphalocrosis spp., Chilo spp., Scirpophaga spp., Lissorhoptrus spp., Oebalus pugnax. The mixtures of the invention are preferably used on rice to control Nilaparvata lugens, Leptocorisa spp., Lissorhoptrus spp., Oebalus pugnax.

The mixtures of the invention may be used on coffee to control, for example, Brevipalpus sp, Hypothenemus Hampei, Perileucoptera Coffeella, Tetranychus spp. The mixtures of the invention are preferably used on coffee to control Hypothenemus Hampei, Perileucoptera Coffeella, Brevipalpus sp, The mixtures of the invention may be used on citrus to control, for example, Panonychus citri, Phyllocoptruta oleivora, Brevipalpus spp., Diaphorina citri, Scirtothrips spp., thrips spp., Unaspis spp., Ceratitis capitata, Phyllocnistis spp., Brevipalpus sp. Aonidiella sp, Parlatoria sp, Ceroplastes sp, Planococcus sp, Pseudococcus sp., Tetranychus sp. Aphis sp. The mixtures of the invention are preferably used on citrus to control Panonychus citri, Phyllocoptruta oleivora, Brevipalpus spp., Diaphorina citri, Scirtothrips spp., thrips spp., Phyllocnistis spp, Brevipalpus sp. Aonidiella sp, Parlatoria sp, Ceroplastes sp, Planococcus sp, Pseudococcus sp., Tetranychus sp., Aphis sp.

The mixtures of the invention may be used on almonds to control, for example, Amyelois transitella, Tetranychus spp.

The mixtures of the invention may be used on fruiting vegetable, including tomatoes, pepper, chili, eggplant, cucumber, squash etc, to control Myzus sp, Aphis sp, thrips spp., Tetranychus spp., Polyphagotarsonemus spp., Aculops spp., Empoasca spp., Spodoptera spp., heliothis spp., Tuta absoluta, Liriomyza spp., Bernisia tabaci, Trialeurodes spp., Paratrioza spp., Frankliniella occidentalis, Frankliniella spp., Anthonomus spp., Phyllotreta spp., Amrasca spp., Epilachna spp., Halyomorpha spp., Scirtothrips spp., Leucinodes spp., Neoleucinodes spp. The mixtures of the invention are preferably used on fruiting vegetable, including tomatoes, pepper, chili, eggplant, cucumber, squash etc, to control, for example, Myzus sp, Aphis sp, thrips spp., Tetranychus spp., Polyphagotarsonemus spp., Aculops spp., Empoasca spp., Spodoptera spp., heliothis spp., Tuta absoluta, Liriomyza spp., Paratrioza spp., Frankliniella occidentalis, Frankliniella spp., Amrasca spp., Scirtothrips spp., Leucinodes spp., Neoleucinodes spp.

The mixtures of the invention may be used on tea to control, for example, Pseudaulacaspis spp., Empoasca spp., Scirtothrips spp., Caloptilia theivora. The mixtures of the invention are preferably used on tea to control Empoasca spp., Scirtothrips spp.

The mixtures of the invention may be used on bulb vegetables, including onion, leek etc to control, for example, thrips spp., Spodoptera spp., heliothis spp. The mixtures of the invention are preferably used on bulb vegetables, including onion, leek etc to control thrips spp.

The mixtures of the invention may be used on grapes to control, for example, Empoasca spp., Lobesia spp., Frankliniella spp., thrips spp., Tetranychus spp., Rhipiphorothrips Cruentatus, Eotetranychus Willamettei, Erythroneura Elegantula, Scaphoides spp, Pseudococcus sp, Planococcus sp The mixtures of the invention are preferably used on grapes to control Frankliniella spp., thrips spp., Tetranychus spp., Rhipiphorothrips Cruentatus, Scaphoides spp, Pseudococcus sp, Planococcus sp The mixtures of the invention may be used on pome fruit, including apples, pairs etc, to control, for example, Cacopsylla spp., Psylla spp., Panonychus ulmi, Cydia pomonella, Quadraspidiotus sp, Lepidosaphes sp, Aphis sp, Dysaphis sp, Eriosoma sp. The mixtures of the invention are preferably used on pome fruit, including apples, pairs etc, to control Cacopsylla spp., Psylla spp., Panonychus ulmi Quadraspidiotus sp, Lepidosaphes sp, Aphis sp, Dysaphis sp, Eriosoma sp The mixtures of the invention may be used on stone fruit to control, for example, Grapholita molesta, Scirtothrips spp., thrips spp., Frankliniella spp., Tetranychus spp., Myzus sp. The mixtures of the invention are preferably used on stone fruit to control Scirtothrips spp., thrips spp., Frankliniella spp., Tetranychus spp., Myzus sp.

The amount of a composition and combination pack of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of pest to be controlled or the application time.

The invention also provides mixtures suitable for resistance management. In particular, the mixtures according to the invention are suitable for controlling insects, for example from the Hemiptera order such as aphids (e.g. Myzus spp), which are resistant to neonicotinoid insecticides. The method comprises applying to said neonicotinoid resistant insects a mixture according to the invention.

The mixtures of the invention are particularly applicable to the control of neonicotinoid resistant insects (and neonicotinoid resistance in insects) of the order Hemiptera, such as: Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi F, Myzus nicotianae, Myzus persicae, Nasonovia ribisnigri, Pemphigus bursarius, Phorodon humuli, Rhopalosiphum insertum Wa, Rhopalosiphum maidis Fitch, Rhopalosiphum padi L., Schizaphis graminum Rond., Sitobion avenae, Toxoptera aurantii, Toxoptera citricola, Phylloxera vitifoliae, Acyrthosiphon dirhodum, Acyrthosiphon solani, Aphis forbesi, Aphis grossulariae, Aphis idaei, Aphis illinoisensis, Aphis maidiradicis, Aphis ruborum, Aphis schneideri, Brachycaudus persicaecola, Cavariella aegopodii Scop., Cryptomyzus galeopsidis, Cryptomyzus ribis, Hyadaphis pseudobrassicae, Hyalopterus amygdali, Hyperomyzus pallidus, Macrosiphoniella sanborni, Metopolophium dirhodum, Myzus malisuctus, Myzus varians, Neotoxoptera sp, Nippolachnus piri Mats., Oregma lanigera Zehnter, Rhopalosiphum fitchii Sand., Rhopalosiphum nymphaeae, Rhopalosiphum sacchari Ze, Sappaphis piricola Okam. +7; Schizaphis piricola, Toxoptera theobromae Sch, and Phylloxera coccinea, Aleurodicus dispersus, Aleurocanthus spiniferus, Aleurocanthus woglumi, Aleurodicus cocois, Aleurodicus destructor, Aleurolobus barodensis, Aleurothrixus floccosus, Bemisia tabaci, Bemisia argentifolli, Dialeurodes citri, Dialeurodes citrifolli, Parabemisia myricae, Trialeurodes packardi, Trialeurodes ricini, Trialeurodes vaporariorum, Trialeurodes variabilis, Agonoscena targionii, Bactericera cockerelli, Cacopsylla pyri, Cacopsylla pyricola, Cacopsylla pyrisuga, Diaphorina citri, Glycaspis brimblecombei, Paratrioza cockerelli, Troza erytreae, Amarasca biguttula biguttula, Amritodus atkinsoni, Cicadella viridis, Cicadulina mbila, Cofana spectra, Dalbulus maidis, Empoasca decedens, Empoasca biguttula, Empoasca fabae, Empoasca vitis, Empoasca papaya, Idioscopus clypealis, Jacobiasca lybica, Laodelphax striatellus, Myndus crudus, Nephotettix virescens, Nephotettix cincticeps, Nilaparvata lugens, Peregrinus maidis, Perkinsiella saccharicida, Perkinsiella vastatrix, Recilia dorsalis, Sogatella furcifera, Tarophagus Proserpina, Zygina flammigera, Acanthocoris scabrator, Adelphocoris lineolatus, Amblypelta nitida, Bathycoelia thalassina, Blissus leucopterus, Clavigralla tomentosicollis, Edessa meditabunda, Eurydema pukhrum, Eurydema rugosum, Eurygaster Maura, Euschistus servus, Euschistus tristigmus, Euschistus heros Helopeltis antonii, Horcias nobilellus, Leptocorisa acuta, Lygus lineolaris, Lygus hesperus, Murgantia histrionic, Nesidiocoris tenuis, Nezara viridula, Oebalus insularis, Scotinophara coarctata, Specific examples of neonicotinoid resistant Hemiptera include Bemisia tabaci, Myzus persicae, Nilaparvata lugens, Aphis gossypii, Trialeurodes vaporariorum, Bactericera cockerelli.

Preferably, the neonicotinoid resistant insects are one or more of as an example Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi F, Myzus nicotianae, Myzus persicae, Nasonovia ribisnigri, Pemphigus bursarius, Phorodon humuli, Rhopalosiphum insertum Wa, Rhopalosiphum maidis Fitch, Rhopalosiphum padi L., Schizaphis graminum Rond., Sitobion avenae, Toxoptera aurantii, Toxoptera citricola, Phylloxera vitifoliae, Bemisia tabaci, Myzus persicae, Nilaparvata lugens, Aphis gossypii, Trialeurodes vaporariorum, Bactericera cockerelli.

More preferably, the neonicotinoid resistant insects are one or more of as an example Bemisia tabaci, Myzus persicae, Nilaparvata lugens, Aphis gossypii, Trialeurodes vaporariorum, Bactericera cockerelli.

The method of the invention comprises applying to the useful plants, the locus thereof or propagation material thereof in admixture or separately, an effective aggregate amount of a compound of formula (I) and one or more polysiloxanes.

The combinations according to the invention have a systemic action and can be used as foliar and soil treatment pesticides.

With the composition and combination pack according to the invention it is possible to inhibit or destroy the pests which occur in plants or in parts of plants (fruit, blossoms, leaves, stems, tubers, roots) in different useful plants, while at the same time the parts of plants which grow later are also protected from attack by pests.

The composition and combination pack of the present invention are of particular interest for controlling pests in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The composition and combination pack according to the invention are applied by treating the pests, the useful plants, the locus thereof, the propagation material thereof, the natural substances of plant and/or animal origin, which have been taken from the natural life cycle, and/or their processed forms, or the industrial materials threatened by pests, attack with a composition and combination pack of compounds of formula (I) and polysiloxane (e.g. according to formula (II)) in an effective amount.

The composition or combination pack according to the invention may be applied before or after infection or contamination of the useful plants, the propagation material thereof, the natural substances of plant and/or animal origin, which have been taken from the natural life cycle, and/or their processed forms, or the industrial materials by the pests.

The composition or combination pack according to the invention can be used for controlling, i.e. containing or destroying, pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these pests.

The formulations according to the invention and the process for their preparation are described by way of example below without the invention being able to be regarded as restricted to these exemplary embodiments.

Where ranges, general formulae or compound classes are stated below, these are intended to include not only the corresponding ranges or groups of compounds which are explicitly mentioned, but also all part ranges and part groups of compounds which can be obtained by removing individual values (ranges) or compounds.

EXAMPLES

The following examples where run with a compound according to formula (I) of the invention (I)

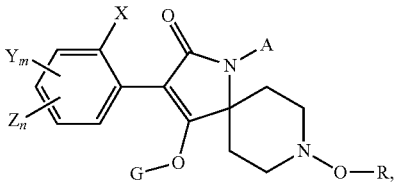

wherein A is methyl, m is 1, n is 1, X is methyl, Y is in the ortho position and is methyl, Z is in the para position and is chloro, G is —(C═O)$OCH_2CH_3$, R is methyl. This compound is referred to as Compound (C) below.

1. Test System 'Efficacy—Aphid (Myzus persicae) Control on Chinese Cabbage'

The efficacies of Compound (C) formulated as SC formulation in combination with different commercially available adjuvants were evaluated in this test. The test was set up as "translaminar test", i.e. mature and horizontally exposed leaves of Chinese cabbage plants were sprayed on top at a rate of 20 g Al/ha. Right after application (2 h AA) a mixed population of Myzus persicae was infested to the bottom side of applied leaves. Three plants per treatment were kept under glasshouse conditions (22° C., 14 h light regime, ca. 60% r.h.). The translaminar efficacy (aphid mortality) was calculated with the aid of Abbott's formula 6 DAA. Results (average of 3 replicates) are shown in Table 1.

TABLE 1

Translaminar efficacy of Compound (C) with different adjuvants 6 DAA

| Tank-mix Adjuvant | mg adj/L | % Mortality., corr. | ST. DEV. |
|---|---|---|---|
| Check | | 0.0 | 0.0 |
| No adjuvant | | 36.7 | 32.1 |
| EW400 | 200 | 97.8 | 1.5 |
| Atplus 463 ® | 500 | 99.0 | 0.5 |
| Atplus 463 ® | 1000 | 99.3 | 0.8 |
| Actirob B ® | 500 | 98.8 | 0.8 |
| Actirob B ® | 1000 | 98.7 | 0.6 |
| Trend 90 ® | 500 | 95.8 | 0.8 |
| Geropon DOS-PG ® | 200 | 99.3 | 0.8 |

TABLE 1-continued

Translaminar efficacy of Compound (C) with different adjuvants 6 DAA

| Tank-mix Adjuvant | mg adj/L | % Mortality., corr. | ST. DEV. |
|---|---|---|---|
| Breakthru ® 5233 | 500 | 98.2 | 0.6 |
| Breakthru ® 5240 | 500 | 97.0 | 1.8 |

Breakthru S233 and S240 are polysiloxane tank-mix adjuvants according to the invention. Specifically Breakthru ® S233 is a non-ionic trisiloxane and Breakthru ® S240 is a polyether modified trisiloxane.
Geropon ® DOS- PG is a Sodium dioctylsulphosuccinate in glycol water solution from Rhodia
Trend 90 ® = Isodecyl alcohol ethoxylate (non-ionic organic surfactants) from DuPont
EW400 = emulsion of rapeseed oil methylester (esterified vegetable oil). This is used as the standard here.
Atplus 463 ® = 60% parafine oil, 40% POE-sorbitol oleat, POE-tridecylalkohol (mineral oils)
Actirob B ® = 95.2% w/w rapeseed oil methylester (esterified vegetable oil)

In the absence of an adjuvant the translaminar aphid control was poor whereas the addition of an adjuvant resulted in full aphid control with all adjuvants. Hence, it can be seen that for the control of aphids which are feeding on the underside of leaves, adjuvants are necessary to improve translaminar efficacy of the active compound.

2. Test System 'Cabbage—Crop Safety (Phytotoxicity)'

The crop safety of Compound (C) formulated as SC formulation in combination with different commercially available adjuvants was evaluated on Chinese cabbage plants. This test was done in parallel to test 1 and plants were of identical quality. Entire plants were sprayed with respective test solutions at a rate of 200 g Al/ha which is ten times higher than the efficacy rate in test 1. The crop safety of the adjuvants alone (without active ingredient) was also evaluated to show that these inherently do not cause phytotoxic reactions in the plant. The adjuvant rate in the blank formulation (without active ingredient) was adjusted to the respective Al rate. The treated foliage was evaluated 7 DAA and 14 DAA for signs of phytoxicity. During this period three plants per treatment were kept under glasshouse conditions (25° C., 14 h light regime, ca. 60% r.h.). The phytotoxicity was assessed as area per leaf affected: 0% means no phytotoxic symptoms were detectable and 50% means half of the leaf area demonstrated phytotoxic reactions like lesions etc.

Average results on phytotoxicity of the tank-mix adjuvants alone are shown in Table 2.

TABLE 2

Crop safety of tank-mix adjuvants solo on Chinese cabbage 7 and 14 DAA

| Tank-mix Adjuvant | mg adj/L | % Phyto 7 DAA | % Phyto 14 DAA |
|---|---|---|---|
| Check | | 0.0 | 0.0 |
| EW400 | 200 | 0.0 | 0.0 |
| Atplus ® 463 | 500 | 0.0 | 0.0 |
| Atplus ® 463 | 1000 | 0.0 | 0.0 |
| Actirob ® B | 500 | 0.0 | 0.0 |
| Actirob ® B | 1000 | 0.0 | 0.0 |
| Breakthru ® S 233 | 500 | 0.0 | 0.0 |
| Breakthru ® S 240 | 500 | 0.0 | 0.0 |
| Trend ® 90 | 500 | 0.0 | 0.0 |
| Geropon ® DOS-PG | 800 | 0.0 | 0.0 |

In Table 2, it is shown that the adjuvants alone do not cause any phytotoxic reactions on the plants.

Average results on phytotoxicity of the different tank-mix adjuvants mixed with Compound (C) are shown in Table 3.

TABLE 3

Crop safety of different tank-mix adjuvants with Compound (C)

| Tank-mix Adjuvant | mg adj/L | % Phyto 7 DAA | % Phyto 14 DAA |
|---|---|---|---|
| Check | | 0 | 0 |
| No adjuvant | | 0.0 | 1.3 |
| EW400 | 200 | 30.0 | 30.0 |
| Atplus ® 463 | 1000 | 30.0 | 30.0 |
| Actirob ® B | 1000 | 31.7 | 33.3 |
| Breakthru ® S 233 | 500 | 0.0 | 3.0 |
| Breakthru ® S 240 | 500 | 2.0 | 5.0 |
| Trend ® 90 | 500 | 0.0 | 0.0 |
| Geropon ® DOS-PG | 800 | 15 | 13.3 |

Surprisingly, at the high rate of 200 g Al/ha, all compositions showed an unacceptable level of phytotoxicity on these glasshouse grown plants, except the compositions of the invention with the Breakthru S233 and S240 polysiloxane adjuvants and the Trend® 90 and Geropon® DOS-PG adjuvants. This is highly surprising, since as shown above in example 1, the combination of the polysiloxane adjuvants and the compound according to formula (I) not only showed almost no phytotoxicity, they also simultaneously provided excellent efficacy against the pests (Table 1). One would have expected, as one has observed with the other adjuvants, that increased efficacy would translate as increased risk of phytoxicity as well. The increase in crop safety of these very efficacious compositions is truly remarkable and could not have been foreseen by the person skilled in the art.

The most preferred adjuvants are Breakthru S233 and S240 polysiloxane adjuvants, which provide surprisingly the least phytotoxicity and the best efficacy combined together with the tetramic acid compounds of this invention.

The invention claimed is:

[1. A pesticidal composition comprising a tetramic acid compound of the formula (I)

(I)

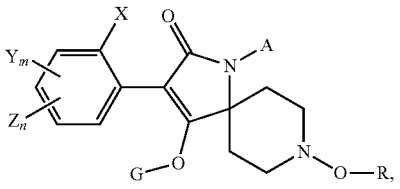

wherein

X, Y and Z independently of each other are $C_{1-4}$alkyl, $C_{3-6}$cycloalkyl, $C_{1-4}$haloalkyl, $C_{1-4}$alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, ammonium, sulfonium or a latentiating group selected from the groups $C_1$-$C_8$alkyl, $C_2$-$C_8$haloalkyl, phenyl$_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, $P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl , $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1C_5$alkylcarbonyl-N—$C_1C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$, alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_5$cyanoalkyl, $C_1$-$C_{10}$nitroalkyl, $C_2$-$C_{10}$aminoalkyl , $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl , $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy, $C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-

$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl , $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio , $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$ -C, alkylthio , $C_1$-$C_3$alkylsulfinyl, $C_1$-$C_3$ alkylsulfonyl, halogen, cyano or by nitro), phenoxy$C_1$-$C_5$alkyl (wherein wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$akylsulfinyl, $C_1$-$C_3$ alkylsulfonyl, halogen, cyano or by nitro), $C_3$-$C_5$-haloalkenyl, $C_1$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy ($C_{1-4}$)alkyl or a group selected from G; and A is hydrogen, $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl,$C_{2-6}$haloalkenyl, $C_{3-6}$alkynyl, $C_{1-4}$cyanoalkyl, benzyl, $C_{1-4}$alkoxy($C_{1-4}$) alkyl, $C_{1-4}$alkoxy ($C_{1-4}$)alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di ($C_{1-6}$alkyl)carbamoyl, benzoyl, $C_{1-6}$alkylsulfonyl, phenylsulfonyl, $C_{1-4}$alkylthio($C_{1-4}$)alkyl, $C_{1-4}$alkylsulfinyl ($C_{1-4}$)alkyl or $C_{1-4}$alkylsulfonyl ($C_{1-4}$)alkyl;

or A is O-$A^1$ wherein $A^1$ is selected from one of A, as defined above, or furanyl -($C_{1-4}$)alkyl, tetrahydro-thiofuranyl, tetrahydro-thiopyranyl or 1-($C_{1-4}$)alkoxy-piperidin-4-yl, or an agrochemically acceptable salt or an N-oxide of formula (I);

and a tank-mix adjuvant selected from the group consisting of polysiloxane(s), sodium dioctylsulphosuccinate, isodecyl alcohol ethoxylate, and mixtures thereof.]

[2. The composition according to claim 1 wherein the compound of formula (I) is selected from compounds wherein R is methyl, X is methyl or methoxy, Y and Z, independently of each other, are methyl, ethyl, methoxy, chloro or bromo, G is hydrogen, methoxycarbonyl or propenyloxycarbonyl or —(C═O)$OCH_2CH_3$, and A is hydrogen, methyl, ethyl, methoxy, ethoxy, methoxymethyl, tetrahydrofuran-2-yl or tetrahydrofuran-3-yl.]

[3. The composition according to claim 1 wherein the compound of formula (I) is selected from compounds wherein m is 1 and n is 1 and Y is in the ortho position and Z is in the para position.]

[4. The composition according to claim 1 wherein the compound of formula (I) is selected from one or more of (i)

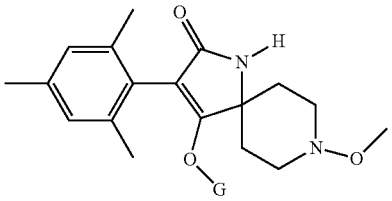

(i')

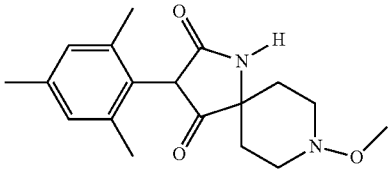

(ii)

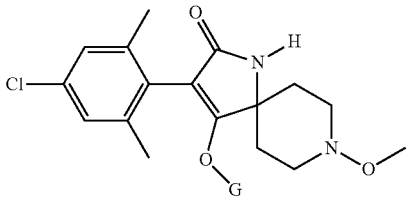

(ii')

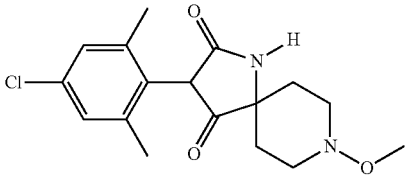

(iii)

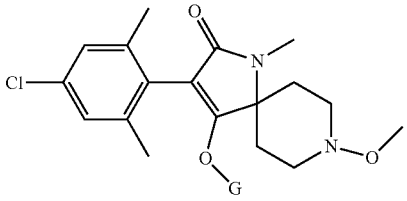

(iii')

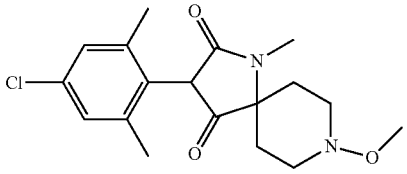

-continued (iv)

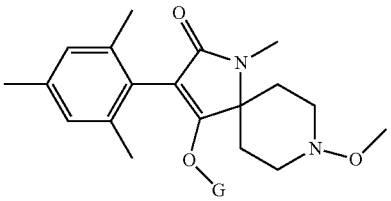

(iv′)

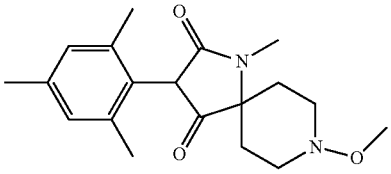

(v)

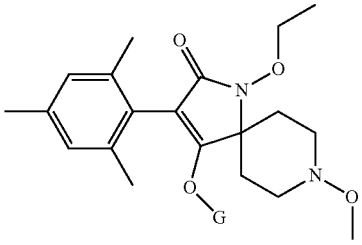

(v′)

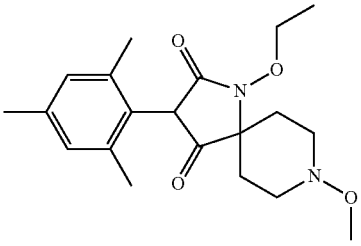

(vi)

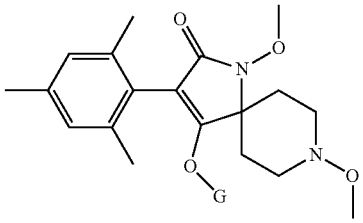

(vi′)

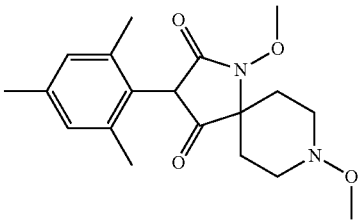

(vii)

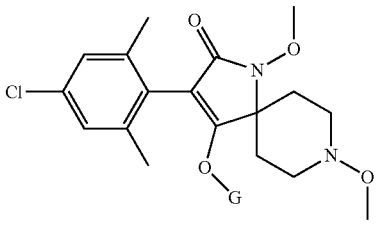

-continued (vii′)

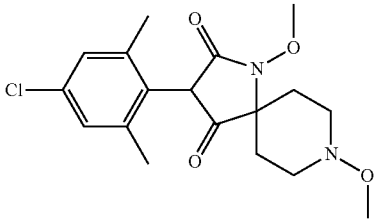

(viii)

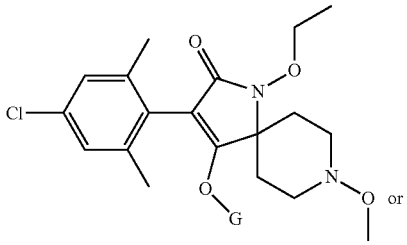

or (viii′)

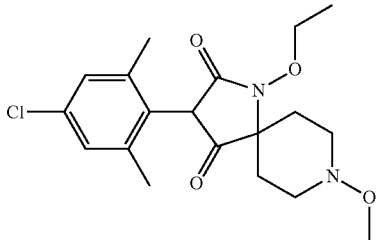

wherein G is

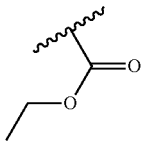

or H.]

[5. The composition according to claim 1 wherein the compound according to formula (I) is formulated as a suspension concentrate, emulsion concentrate, wettable powder, water dispersible granule, soluble liquid, emulsion in water, oil dispersion, soluble granule or soluble powder.]

[6. The composition according to claim 1 wherein the adjuvant is a polysiloxane selected according to formula (II)

(II)

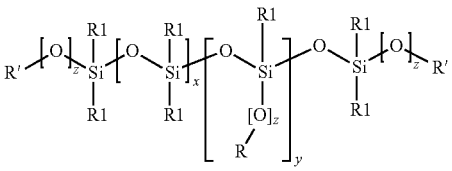

wherein z is 0 or 1 x is a number from 0 to 100 y is 0 or greater

R' is R or an alkyl radical having 1 to 8 carbon atoms or a hydrogen atom

R is $C_nH_{2n}O(C_eH_{2e}O)_pK$ or $Si_nR1_{2n}O(Si_eR1_{2e}O)_pK$

R1 are independently alkyl, alkenyl or alkynyl radicals having 1 to 4 carbon atoms or aryl radicals n is 1, 2, 3, 4 or greater e is 1, 2, 3, 4 or greater p is 0 or greater K is H, an alkyl radical having at most 4 carbon atoms or $SiR1_2R2$, wherein R2 is hydrogen or an alkyl radical having at most 4 carbon atoms.]

[7. The composition according to claim 1 wherein the adjuvant is a polysiloxane selected according to formula (II')

(II')

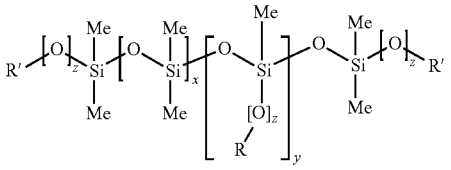

wherein z is 0 or 1 x is a number from 0 to 100 y is 0 or greater

R' is R or an alkyl radical having 1 to 8 carbon atoms or a hydrogen atom

R is $C_nH_{2n}O(C_eH_{2e}O)_pK$ n is 3 or 4 e is 2, 3 or 4 p is 3 or greater

K is H or an alkyl radical having at most 4 carbon atoms.]

[8. A combination pack comprising a combination of a compound according to formula (I) as defined in claim 1 and an adjuvant selected from the group consisting of polysiloxane(s), sodium dioctylsulphosuccinate, isodecyl alcohol ethoxylate, and mixtures thereof, wherein a first container contains the compound according to formula (I) and a second container contains the said adjuvant.]

[9. The combination pack according to claim 8 wherein the adjuvant is a polysiloxane selected according to formula (II)

(II)

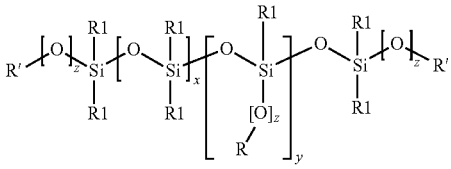

wherein z is 0 or 1 x is a number from 0 to 100 y is 0 or greater

R' is R or an alkyl radical having 1 to 8 carbon atoms or a hydrogen atom

R is $C_nH_{2n}O(C_eH_{2e}O)_pK$ or $Si_nR1_{2n}O(Si_eR1_{2e}O)_pK$

R1 are independently alkyl, alkenyl or alkynyl radicals having 1 to 4 carbon atoms or aryl radicals n is 1, 2, 3, 4 or greater e is 1, 2, 3, 4 or greater p is 0 or gr K is H, an alkyl radical having at most 4 carbon atoms or $SiR1_2R2$, wherein R2 is hydrogen or an alkyl radical having at most 4 carbon atoms.]

[10. The combination pack according to claim 9 wherein the adjuvant is a polysiloxane is selected according to formula (II')

(II')

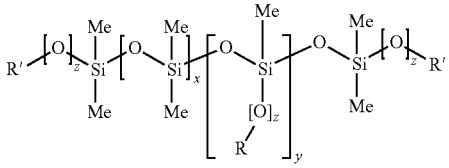

wherein z is 0 or 1 x is a number from 0 to 100 y is 0 or greater

R' is R or an alkyl radical having 1 to 8 carbon atoms or a hydrogen atom

R is $C_nH_{2n}O(C_eH_{2e}O)_pK$ n is 3 or 4 e is 2, 3 or 4 p is 3 or greater

K is H or an alkyl radical having at most 4 carbon atoms.]

*11. A pesticidal composition comprising a tetramic acid compound of the formula (I):*

*(I)*

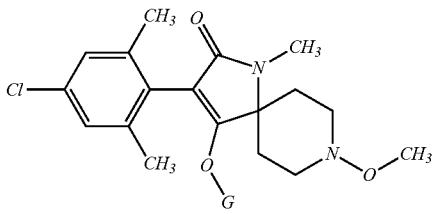

*wherein G is*

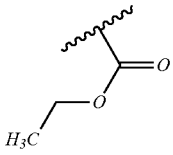

*or H;*

*or an agrochemically acceptable salt or an N-oxide of formula (I);*

*and a tank-mix adjuvant selected from one or more of: polysiloxane(s), sodium dioctylsulphosuccinate, and isodecyl alcohol ethoxylate.*

*12. The composition according to claim 11, wherein G is*

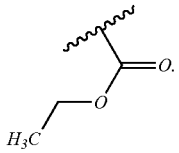

*13. The composition according to claim 11, wherein the compound according to formula (I) is formulated as a*

*suspension concentrate, emulsion concentrate, wettable powder, water dispersible granule, soluble liquid, emulsion in water, oil dispersion, soluble granule or soluble powder.*

*14. The composition according to claim 11, wherein the adjuvant is a polysiloxane selected according to formula (II)*

(II)

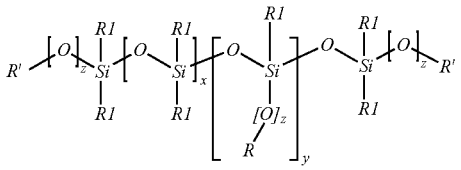

*wherein*

*z is 0 or 1;*

*x is a number from 0 to 100;*

*y is 0 or greater;*

*R' is R or an alkyl radical having 1 to 8 carbon atoms or a hydrogen atom;*

*R is* $C_nH_{2n}O(C_eH_{2e}O)_pK$ *or* $Si_eR1_{2n}O(Si_eR1_{2n}O)_pK$*;*

*R1 are independently alkyl, alkenyl or alkynyl radicals having 1 to 4 carbon atoms or aryl radicals;*

*n is 1, 2, 3, 4 or greater;*

*e is 1, 2, 3, 4 or greater;*

*p is 0 or greater;*

*K is H, an alkyl radical having at most 4 carbon atoms or* $SiR1_2R2$*, wherein R2 is hydrogen or an alkyl radical having at most 4 carbon atoms.*

*15. A combination pack comprising a combination of a compound according to formula (I) as defined in claim 11 and an adjuvant selected from one or more polysiloxane(s), sodium dioctylsulphosuccinate, and isodecyl alcohol ethoxylate;*

*wherein a first container contains the compound according to formula (I) and a second container contains said adjuvant.*

*16. The combination pack according to claim 15, wherein the adjuvant is a polysiloxane according to formula (II)*

(II)

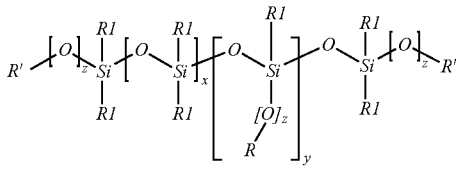

*wherein*

*z is 0 or 1;*

*x is a number from 0 to 100;*

*y is 0 or greater;*

*R' is R or an alkyl radical having 1 to 8 carbon atoms or a hydrogen atom;*

*R is* $C_nH_{2n}O(C_eH_{2e}O)_pK$ *or* $Si_nR1_{2n}O(Si_eR1_{2e}O)_pK$*;*

*R1 are independently alkyl, alkenyl or alkynyl radicals having 1 to 4 carbon atoms or aryl radicals;*

*n is 1, 2, 3, 4 or greater;*

*e is 1, 2, 3, 4 or greater;*

*p is 0 or greater; and*

*K is H, an alkyl radical having at most 4 carbon atoms or* $SiR1_2R2$*, wherein R2 is hydrogen or an alkyl radical having at most 4 carbon atoms.*

* * * * *